(12) United States Patent
Hearing et al.

(10) Patent No.: US 9,168,297 B2
(45) Date of Patent: Oct. 27, 2015

(54) REGULATION OF SKIN PIGMENTATION BY NEUREGULIN-1 (NRG-1)

(75) Inventors: Vincent J. Hearing, Leesburg, VA (US); Wonseon Choi, Chevy Chase, MD (US); Ludger Kolbe, Dohren (DE); Rainer Wolber, Hamburg (DE)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 155 days.

(21) Appl. No.: 13/805,638

(22) PCT Filed: Jun. 23, 2011

(86) PCT No.: PCT/US2011/041610
§ 371 (c)(1),
(2), (4) Date: Dec. 19, 2012

(87) PCT Pub. No.: WO2011/163466
PCT Pub. Date: Dec. 29, 2011

(65) Prior Publication Data
US 2013/0095053 A1    Apr. 18, 2013

Related U.S. Application Data

(60) Provisional application No. 61/357,846, filed on Jun. 23, 2010.

(51) Int. Cl.
| | | |
|---|---|---|
| *A61K 38/00* | (2006.01) | |
| *A61K 38/17* | (2006.01) | |
| *A61K 38/18* | (2006.01) | |
| *A61K 39/395* | (2006.01) | |
| *C07K 14/475* | (2006.01) | |
| *A61K 31/7105* | (2006.01) | |
| *A61K 38/08* | (2006.01) | |
| *A61K 38/10* | (2006.01) | |

(52) U.S. Cl.
CPC ......... *A61K 39/3955* (2013.01); *A61K 31/7105* (2013.01); *A61K 38/08* (2013.01); *A61K 38/10* (2013.01); *A61K 38/1883* (2013.01); *C07K 14/4756* (2013.01)

(58) Field of Classification Search
None
See application file for complete search history.

(56) References Cited

U.S. PATENT DOCUMENTS 7,226,907 B1 *  6/2007  Zhou .............................. 514/7.5
7,429,489 B2     9/2008  Peled et al.

OTHER PUBLICATIONS

Pettit et al. (1998). Trends Biotechnol. 16:343-349.*
Adameyko et al., "Schwann cell precursors from nerve innervation are a cellular origin of melanocytes in skin," *Cell*, 139(2):366-79, Oct. 16, 2009.
Britsch et al., "The transcription factor Sox10 is a key regulator of peripheral glial development," *Genes Dev.*, 15(1):66-78, 2001.
Buac et al., "NRG1/ERBB3 signaling in melanocyte development and melanoma: inhibition of differentiation and promotion of proliferation," *Pigment Cell & Melanoma Research*, 22(6):773-84, Dec. 2009.
Carraway et al., "An intramembrane modulator of the ErbB2 receptor tyrosine kinase that potentiates neuregulin signaling," *J. Biol. Chem.*, 274:5263-66, 1999.
Esper et al., "Neuregulins: versatile growth and differentiation factors in nervous system development and human disease," *Brain Res. Rev.* 51:161-75, 2006.
Falls et al., "Neuregulins: functions, forms, and signaling strategies," *Exp. Cell. Res.*, 284:14-30, 2003.
Fernandez et al., "Neuregulin/ErbB3 signaling affects early melanocyte development," Pigment Cell & Melanoma Research, vol. 21, No. 2, p. 310, Abstract only, Apr. 2008.
Gordon-Thomson et al., "ErbB receptors mediate both migratory and proliferative activities in human melanocytes and melanoma cells," *Melanoma Res.*, 15(1):21-8, 2005.
International Search Report and Written Opinion issued Aug. 17, 2011 by the European Patent Office for International Patent Application No. PCT/US2011/041610, filed Jun. 23, 2011, 12 pp.
Stove et al., "Bowes melanoma cells secrete heregulin, which can promote aggregation and counteract invasion of human mammary cancer cells," *Int. J. Cancer*, 114:572-8, 2005.
Stove et al., "The heregulin/human epidermal growth factor receptor as a new growth factor system in melanoma with multiple ways of deregulation," *J Invest. Dermatol.*, 121:802-12, 2003.

* cited by examiner

*Primary Examiner* — Christine J Saoud
*Assistant Examiner* — Jon M Lockard
(74) *Attorney, Agent, or Firm* — Klarquist Sparkman, LLP

(57) ABSTRACT

Disclosed herein are compositions and methods of using such compositions to modulate pigmentation and proliferation of a melanocyte, such as to prevent or treat skin disorders, including skin cancer or for use for cosmetic purposes. In one example, a method of modulating pigmentation of a melanocyte includes contacting the melanocyte (such as a human melanocyte) with an agent that modulates neuregulin-1 (NRG-1) activity, such as an agent that increases or decreases NRG-1 activity, thereby modulating pigmentation of the melanocyte. In one particular example, the method of increasing melanocyte pigmentation or proliferation can be used to reduce UV skin damage, including that associated with skin cancer. In another example, the method of decreasing melanocyte pigmentation can be used to treat a skin pigmentation disorder associated with undesired increased skin pigmentation.

6 Claims, 15 Drawing Sheets

FIG. 2A
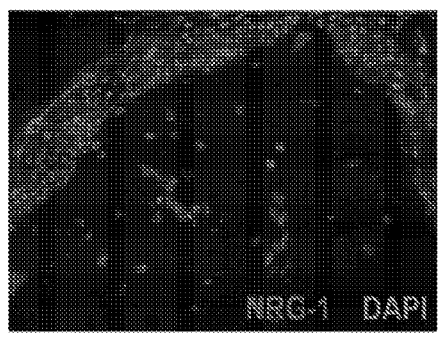 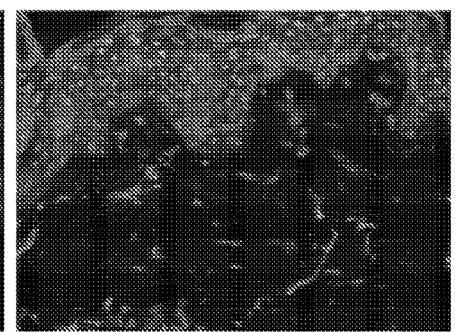
FIG. 2B
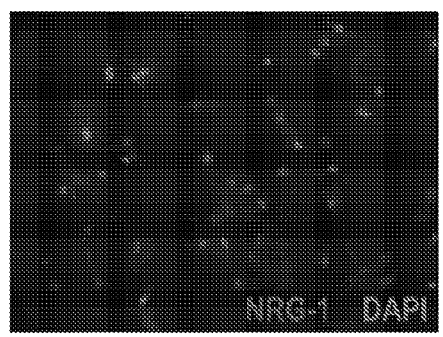 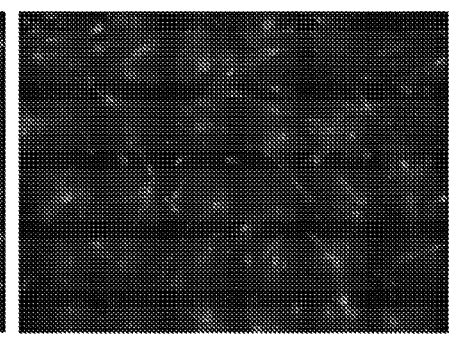
FIG. 2C
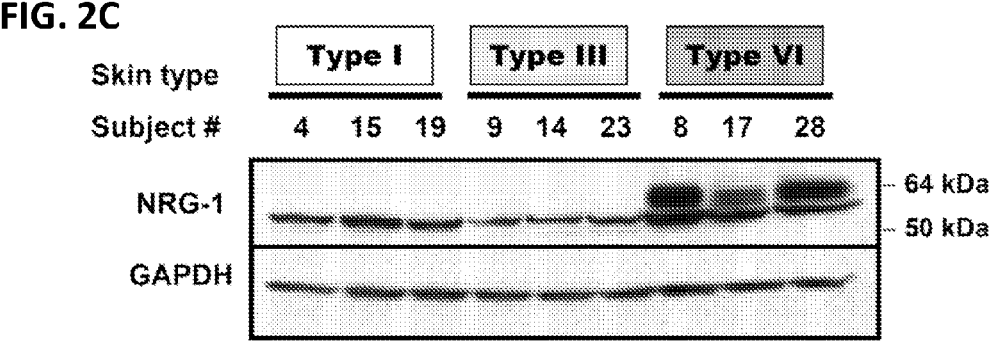

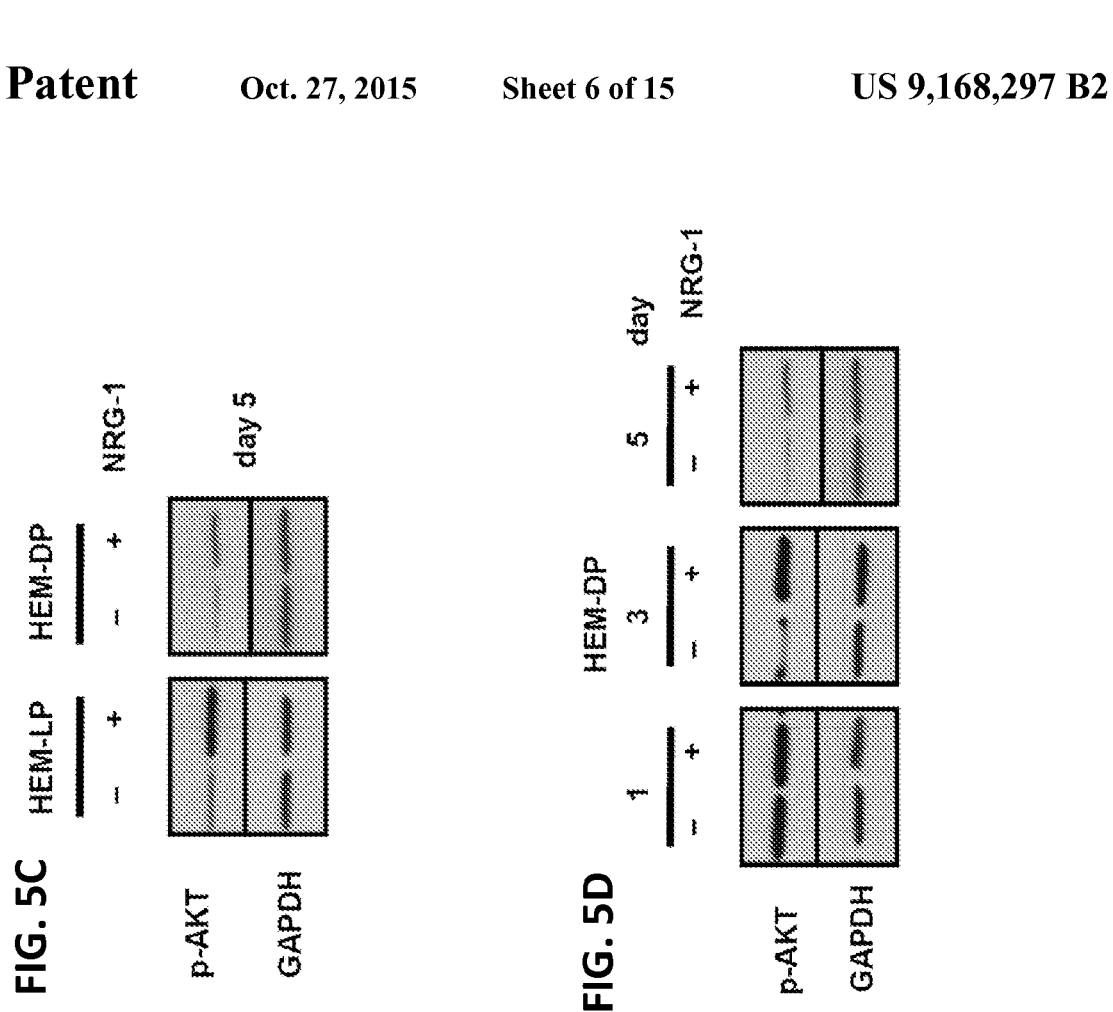
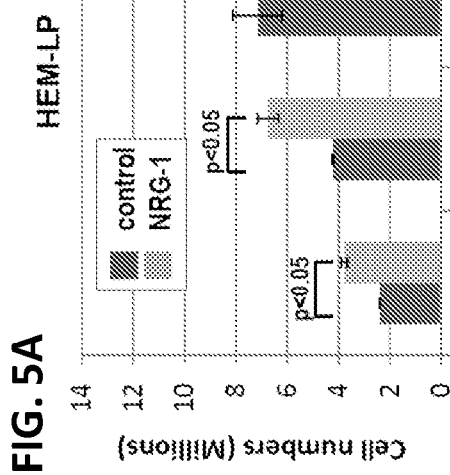
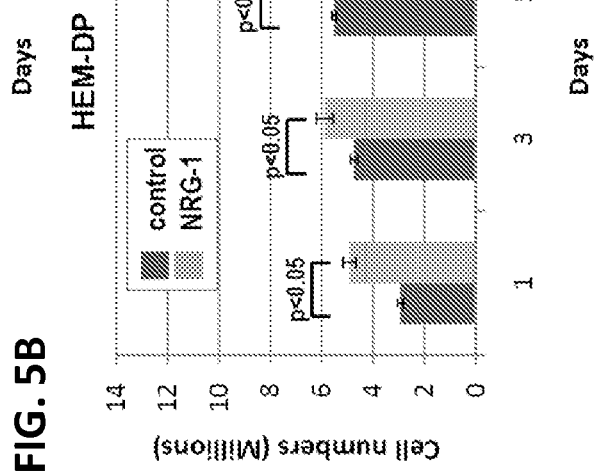

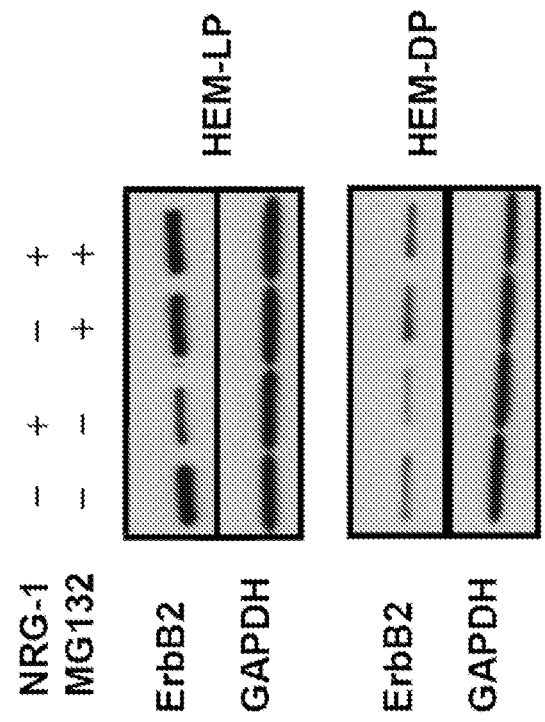
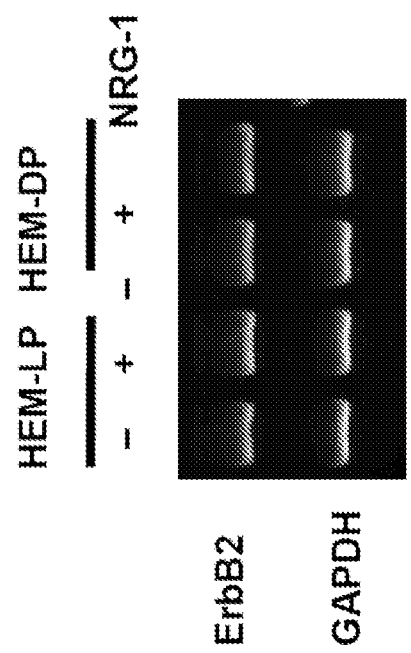

FIG. 12

EGF-domain of NRG-1

SEQ ID NO 9: CVNGGECFMVKDLSNPSRYLCKCQPGFTGARC

SEQ ID NO 10: CVNGGECFMVKDLSNPSRYLCKCPNEFTGDRC

Design of 16-mer peptides

WC-01: H-CVNGGECFMVKDLSNP-OH
WC-02: H-FMVKDLSNPSRYLCKC-OH
WC-03: H-SRYLCKCQPGFTGARC-OH
WC-04: H-SRYLCKCPNEFTGDRC-OH
WC-05: H-CVNGGECFMVKDLSNPSRYLCKCPNEFTGDRC-OH

TSHLVKCAEKEKTFCVNGGECFMVKDLSNPSRYLCKCPNEFTGDRCQNYVMASFYK
HLGIEFMEAEELYQK (SEQ ID NO: 11)

REGULATION OF SKIN PIGMENTATION BY NEUREGULIN-1 (NRG-1)

CROSS REFERENCE TO RELATED APPLICATION APPLICATIONS

This is the U.S. National Stage of International Application No. PCT/US2011/041610, filed Jun. 23, 2011, which was published in English under PCT Article 21(2), which in turn claims the benefit of U.S. Provisional Application No. 61/357,846, filed Jun. 23, 2010, which is incorporated herein by reference in its entirety.

FIELD OF THE DISCLOSURE

This disclosure relates to the field of skin pigmentation and in particular, to methods for regulating melanocyte proliferation and/or pigmentation with neuregulin (e.g., NRG-1) to prevent or treat pigmentary skin disorders (such as skin cancer) and/or for cosmetic reasons.

BACKGROUND

The constitutive color of human skin varies widely among different ethnic groups and is frequently classified into one of six distinct skin phototypes, the most commonly used method to categorize skin color depending on its ability to tan or to burn following exposure to ultraviolet (UV) radiation. UV radiation stimulates the expression and function of many melanocyte-specific proteins, such as tyrosinase (TYR), tyrosinase-related protein 1 (TYRP1), dopachrome tautomerase (DCT) and melanoma antigen recognized by T-cells 1 (MART1). The observed increases are typically more dramatic in darker skin types than in lighter skin types. Despite that diversity, the density of melanocytes in all types of skin is virtually identical and the differences in visible skin color depend on a number of factors including the amount of melanin produced, the efficiency of their transfer from melanocytes to keratinocytes, and the ratio of pheomelanin to eumelanin synthesized. Levels of constitutive skin pigmentation not only have dramatic social and cosmetic consequences, but also are closely and inversely correlated with the risk of skin cancers.

SUMMARY OF THE DISCLOSURE

It is disclosed herein that melanogenic factors secreted from fibroblasts regulate constitutive skin color and possibly its dysfunction in pigmentary skin diseases. One of these secreted factors, NRG-1, was observed to be highly expressed by fibroblasts derived from darker skin. NRG-1 was also observed to significantly increase pigmentation in a reconstructed skin model and in melanocytes, indicating its role in regulating the constitutive color of different phototypes of skin and their responses to the environment, particularly via factors they secrete.

Based on these observations, compositions and methods of modulating pigmentation and proliferation of melanocytes with such compositions (as well as with known NRG-1 modulatory agents) are disclosed. In one example a composition includes an agent that specifically modulates skin pigmentation or proliferation, such as increases (e.g., an NRG-1 agonist) or decreases (e.g., an NRG-1 inhibitor) pigmentation. In one example, an agent is an NRG-1 peptide which is a fragment of native NRG-1 or a variant thereof that retains biological activity, such as modulating (e.g., increasing or decreasing) melanocyte proliferation or pigmentation, including but not limited to capable of activating ERBB. In one example, an NRG-1 fragment can include an extracellular domain of NRG-1 containing the receptor-binding epidermal growth factor (EGF)-like domain.

Also provided are pharmaceutical compositions including any of the disclosed peptides and a pharmaceutically acceptable carrier. In one example, the pharmaceutical composition is for use in the manufacture of a medicament or for use as a medicament. Also are kits including at least one of the pharmaceutical compositions and including instructions regarding use of compositions. In one example, the kit includes a composition, applicator, such as for applying the composition to the surface to be treated and instructions. In one example, the kit is a kit for reducing UV skin damage and includes one or more sunscreen agents with one or more of the disclosed compositions.

Methods of use of the disclosed peptides are also provided, such as methods of modulating pigmentation, proliferation or a combination thereof of a melanocyte. In some examples, a method of modulating pigmentation of melanocytes can include contacting the melanocyte (such as a human melanocyte) with a composition including an agent that modulates NRG-1 activity, such as an agent that increases (e.g., an NRG-1 coding sequence or a functional fragment thereof, or a NRG-1 protein or functional fragment thereof) or decreases (e.g., an NRG-1 inhibitory RNA molecule or NRG-1 inhibitory antibody) NRG-1 activity (such as NRG-1 nucleic acid expression, NRG-1 protein expression, or NRG-1 protein biological activity), thereby modulating pigmentation of the melanocyte. In one example, the method of increasing melanocyte pigmentation or proliferation can be used to prevent or reduce UV skin damage and skin cancer. In another example, the method of decreasing melanocyte pigmentation can be used to treat a skin pigmentation disorder associated with undesired increased skin pigmentation. In other examples, the method of regulating melanocyte pigmentation or proliferation can be used for cosmetic purposes, such as to lighten or darken a subject's skin color.

Also disclosed are methods of treating a skin cancer, such as melanoma. Methods of treating a melanoma can include administering to a subject, such as a human, a therapeutically effective amount of a composition including an agent that decreases NRG-1 activity (such as an NRG-1 inhibitory RNA molecule or NRG-1 inhibitory antibody) in a melanoma cell as compared to NRG-1 activity in such cell in the absence of the agent, thereby treating one or more signs or symptoms associated with the melanoma.

The foregoing and other features of the disclosure will become more apparent from the following detailed description of a several embodiments which proceeds with reference to the accompanying figures.

BRIEF DESCRIPTION OF THE FIGURES

FIGS. 2A-2C are digital images illustrating protein expression of NRG-1 in normal human skin and by cultured normal human fibroblasts. FIG. 2A) Frozen sections of normal human skin from type I and type VI phototypes were used to examine expression levels of NRG-1. Images are representative of 3 different subjects of each phototype, which all showed similar results. FIG. 2B) Fibroblasts were cultured in chamber-slides and stained with NRG-1 antibody. Images are representative of 3 different fibroblast cell lines of each phototype, which all showed similar results. FIG. 2C) Proteins were extracted from each of 15 fibroblast cell lines and western blotting was used to detect the level of NRG-1 and GAPDH (used as a loading control). Three representative fibroblast lines per each of 3 skin types are shown.

FIG. 3A) Light (from Caucasian skin, n=1), Medium (from Asian skin, n=4) and Dark (from African-American skin, n=2). Melanoderms were treated with or without NRG-1 (50 ng/ml) for 9 days. Images were taken of the inverted Melanoderms at the end of the protocol. The L value shown for each Melano-Derm was calculated by the average of 3 spots measured in the center of each Melanoderm; results are the averages of L values in the number of studies indicated above±SD. FIG. 3B) Melanin content in human skin equivalents analyzed by Fontana-Masson staining; insets show areas at 3-fold magnification. FIG. 3C) Overhead bright field microscopic view of Melanoderms; insets show areas at 3-fold magnification.

FIG. 4A illustrates mRNA levels and FIG. 4B protein levels of NRG-1 in 3 different fibroblasts (#8, 17, and 28) from type VI skin after control shRNA ("C") or NRG-1 shRNA ("N") transduction. FIG. 4C shows change of MelanoDerm pigmentation when fibroblasts were transduced with control shRNA or NRG-1 shRNA. L values shown are the average of 3 spots measured in the center of each Melanoderm.

FIGS. 5A-5D illustrate the effect of NRG-1 on the proliferation of human melanocytes in culture. FIG. 5A) Lightly-pigmented (HEM-LP) and FIG. 5B) darkly-pigmented (HEM-DP) melanocytes were treated with or without NRG-1 (50 ng/ml) for 1, 3, 5 or 9 days in 10 cm culture dishes and total cell numbers were counted. Results are the averages of three studies±SD. FIG. 5C) Phosphorylated-Akt levels were detected by western blotting for HEM-LP and HEM-DP melanocytes treated with NRG-1 (50 ng/ml) for 5 days compared to vehicle treated controls; GAPDH is used as a loading control. FIG. 5D) HEM-DP melanocytes were treated with NRG-1 (50 ng/ml) for 1, 3 or 5 days and p-Akt levels were detected by western blotting compared to vehicle treated controls; GAPDH is used as a loading control. Results shown are representative of three studies; statistically significant differences are indicated.

FIG. 6A) Lightly-pigmented (HEM-LP) and FIG. 6B) Darkly-pigmented (HEM-DP) melanocytes were treated with or without NRG-1 (50 ng/ml) for 1, 3, 5 or 9 days and proteins were extracted from each sample. After centrifugation at 10,000 g for 15 minutes, precipitates were analyzed for melanin content, and the supernatants were analyzed for protein content. Results are the average of three studies±SD; statistically significant differences are indicated.

FIG. 7A) HEM-LP and HEM-DP melanocytes were treated with or without NRG-1 (50 ng/ml) for 5 days, and levels of ERBB2, ERBB3 or ERBB4 were detected by western blotting. Results shown are representative of three studies. FIG. 7B) Expression of ERBB2 was examined in HEM-LP and in HEM-DP melanocytes after 1 or 9 days or treatment with NRG-1 compared to vehicle-treated controls; the results are representative of two independent studies.

FIGS. 8A and 8B are digital images illustrating the mechanism of ERBB2 abrogation after NRG-1 treatment. FIG. 8A) ERBB2 mRNA levels in HEM-LP and in HEM-DP melanocytes were detected by RT-PCR after treatment with or without NRG-1 (50 ng/ml) for 1 day. FIG. 8B) MG132 (120 nM) was added to the melanocyte culture medium to inhibit proteasomal degradation during treatment of HEM-LP and HEM-DP melanocytes with or without NRG-1 (50 ng/ml). Proteins were extracted for each sample, and ERBB2 levels were detected by western blotting. Results are representative of three studies.

FIG. 9A) HEM-DP melanocytes were treated for 9 days with 50 ng/ml NRG-1 in the presence of C39 (0.5 µM) or CI-1033 (2 µM) or vehicle (DMSO) alone. The results are the averages of 3 independent studies±SD. FIG. 9B) Dark (from African-American skin) MelanoDerms were treated for 9 days with 50 ng/ml NRG-1 in the presence of C39 (0.5 µM) or CI-1033 (2 µM) or vehicle (DMSO) alone. L values shown are the average of 3 spots measured in the center of each Melanoderm.

FIG. 12 is a schematic including the following: (1) a sequence alignment of two EGF-domains of NRG-1 set forth as SEQ ID NOs: 9 and 10; (2) 16-mer NRG-1 peptides including various portions of SEQ ID NO: 9 or 10; and (3) the amino acid sequence (SEQ ID NO: 11) of a commercially available NRG-1. In particular, WC-01 is a 16-mer NRG-1 peptide including amino acids 1-16 of SEQ ID NO: 9 or SEQ ID NO: 10. WC-02 is a 16-mer NRG-1 peptide including amino acids 17-32 of SEQ ID NO: 9. WC-03 is a 16-mer NRG-1 peptide including amino acids 8-23 of SEQ ID NO: 9. WC-04 is a 16-mer NRG-1 peptide including amino acids 17-32 of SEQ ID NO: 10.

SEQUENCE LISTING

Figure 1:
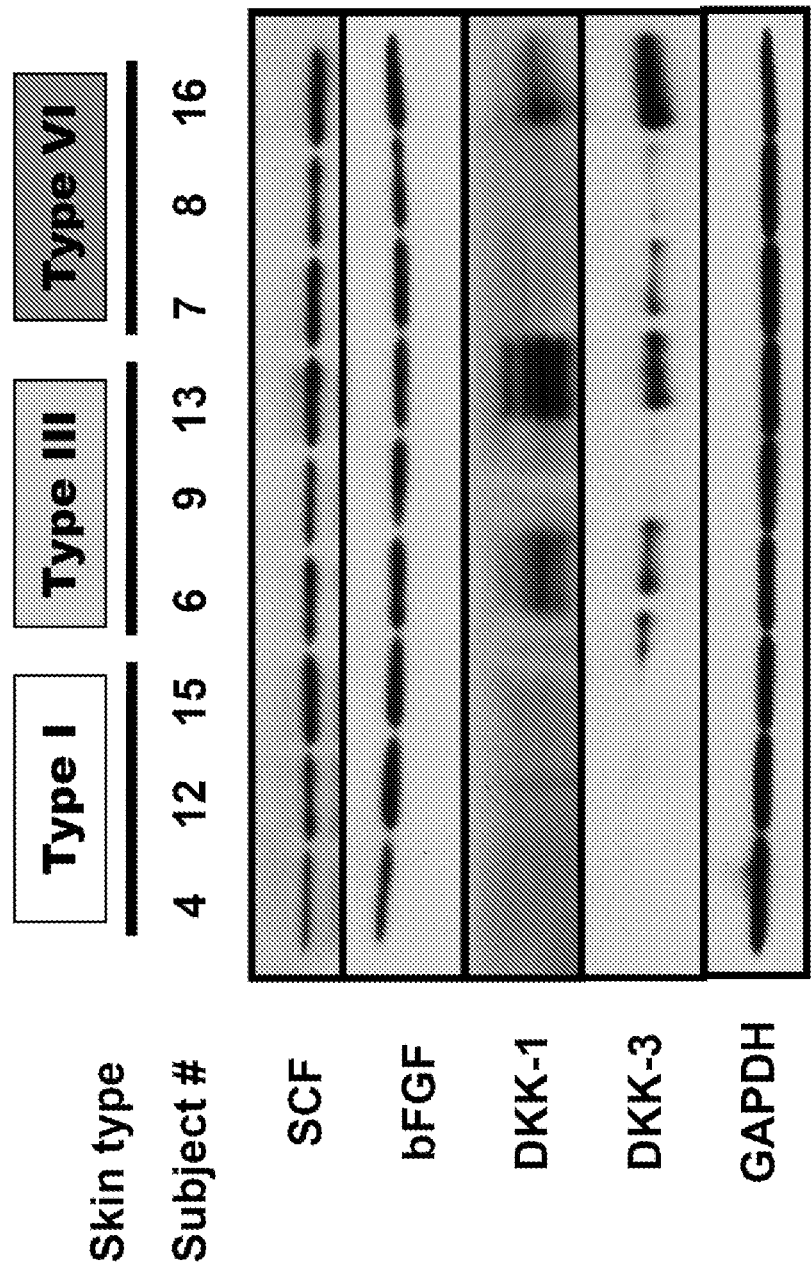
FIG. 1 is a digital image illustrating protein expression levels of known fibroblast-derived melanogenic paracrine factors. Proteins were extracted from each of the 15 fibroblast cell lines, and western blotting was used to detect levels of SCF, bFGF, DKK-1, DKK-3 and GAPDH (used as a loading control). Three representative fibroblast lines per each of 3 skin types are shown.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is the nucleotide sequence of sense human ERBB2 primer.

SEQ ID NO: 2 is the nucleotide sequence of antisense human ERBB2 primer.

SEQ ID NO: 3 is the nucleotide sequence of sense NRG-1 primer.

SEQ ID NO: 4 is the nucleotide sequence of antisense NRG-1 primer.

SEQ ID NO: 5 is the nucleotide sequence of sense glyceraldehyde-3-phosphate dehydrogenase (GAPDH) primer.

SEQ ID NO: 6 is the nucleotide sequence of antisense GAPDH primer.

SEQ ID NO: 7 is an amino acid sequence of human Type 1 NRG-1.

SEQ ID NO: 8 is a nucleotide sequence of human Type 1 NRG-1.

SEQ ID NO: 9 is an amino acid sequence of an EGF-domain of NRG-1.

SEQ ID NO: 10 is an amino acid sequence of an EGF-domain of NRG-1.

SEQ ID NO: 11 is an amino acid sequence of a commercially available NRG-1 peptide (bold amino acids corresponding to EGF domain).

DETAILED DESCRIPTION OF SEVERAL EMBODIMENTS

I. Introduction

Human skin pigmentation is regulated by complex and intricate interactions among melanocytes and keratinocytes in the epidermis and fibroblasts in the dermis. A number of factors secreted from keratinocytes and/or from fibroblasts have been shown to be involved in regulating skin pigmentation after UV exposure. For example, DKK-1 is a regulator of topological skin color (palmoplantar vs. non-palmoplantar skin). The gene expression patterns of fibroblasts in different anatomical locations are remarkably distinct and are also stable even after the cells are put into culture. For example, a remarkable diversity in gene expression patterns in fibroblasts derived from different phototypes of skin (I, III and VI) was revealed in the present studies and there was great consistency in those expression patterns in different individuals.

To investigate the role of fibroblasts (particularly proteins they secrete) in regulating the constitutive color of different phototypes of skin and their responses to the environment, the inventors used cDNA microarray analysis to identify novel melanogenic factors secreted from fibroblasts derived from lighter skin types compared to darker skin types. The inventors identified 12 differentially regulated secreted factors in fibroblasts derived from type VI skin compared to fibroblasts derived from types I or III skin that might play a role in regulating the constitutive skin colors of different skin phototypes. Different phototypes of skin show different characteristics such as their ability to tan, burn and/or genetic predispositions to skin cancers. For example, the Fitzpatrick Classification Scale classifies a person's complexion and their tolerance of sunlight. It is used by many practitioners to determine how someone will respond or react to facial treatments, and how likely they are to get skin cancer. The Fitzpatrick Classification Scale is set forth in the Table below.

| Skin Type | Skin Color | Characteristics |
|---|---|---|
| I | White; very fair; red or blond hair; blue eyes; freckles | Always burns, never tans |
| II | White; fair; red or blond hair; blue, hazel, or green eyes | Usually burns, tans with difficulty |
| III | Cream white; fair with any eye or hair color; very common | Sometimes mild burn, gradually tans |
| IV | Brown; typical Mediterranean Caucasian skin | Rarely burns, tans with ease |
| V | Dark Brown; mid-eastern skin types | very rarely burns, tans very easily |
| VI | Black | Never burns, tans very easily |

One of the secreted factors, NRG-1, was observed to be highly expressed by fibroblasts derived from darker skin (type VI skin). NRGs are signaling proteins that bind to the extracellular domain of the receptor tyrosine kinase ERBB3 and ERBB4, thereby activating cellular signaling pathways. NRGs are a diverse group of secreted peptide growth factors that mediate cell-cell interactions in the nervous system, heart, breast, and other organ systems, signaling through tyrosine kinase receptors of the ERBB family. NRG-1 is the term for a family of proteins derived by alternative splicing from a single gene, which function as ligands for the receptors ERBB3 and ERBB4, and the calcium-binding EGF-like domain is sufficient for the activation of ERBB receptor-tyrosine kinases. Many isoforms of NRG-1 protein of various sizes have been reported, e.g. 140, 110, 95, 60, 55 and 45 kDa. NRG-1 is expressed in brain and in nervous tissues and is involved in the differentiation, migration and development of neurons and for dendritic development.

NRG-1 was investigated for its potential to regulate pigmentation in the MelanoDerm skin model and in cultured human melanocytes. Exogenous rh-NRG-1 was demonstrated to be able to increase pigmentation both in melanocyte culture and in the MelanoDerm skin model. Furthermore, only fibroblasts derived from type VI skin expressed the 60-kDa isoform of NRG-1, and when that isoform of NRG-1 was knocked-down in fibroblasts, the darkening effect of fibroblasts derived from type VI skin was significantly decreased. Overall, these results strongly support that NRG-1 is a melanogenic factor regulating the constitutive pigmentation of darker human skin.

Based on these observations, disclosed herein are compositions and methods for regulating NRG-1 expression in the skin as a means to regulate pigmentation and proliferation of melanocytes. For example, the use of NRG-1 inhibitors, such as inhibitory RNAs or inhibitor antibodies, can be used to reduce melanocyte proliferation and/or pigmentation, for example to reduce undesired darker skin pigmentation or melanoma. Alternatively, NRG-1 agonists, such as fragments of NRG-1 or variants thereof, can be used to increase melanocyte proliferation and/or pigmentation, for example to protect the skin from UV damage, such as that which causes skin cancer, or for cosmetic purposes such as to darken ones skin color.

II. Abbreviations and Terms

BSA: bovine serum albumin
DMEM: Dulbecco's modified Eagle medium
EGF: Epidermal Growth Factor
FBS: fetal bovine serum
HEM-DP: human epidermal melanocytes, darkly pigmented HEM-LP: human epidermal melanocytes, lightly pigmented
MAPK: mitogen-activated protein kinase
NRG: neuregulin
PBS: phosphate buffered saline
PI-3K: phosphatidylinositol-3-kinase
TBS: Tris buffered saline
UV: ultraviolet The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an agent" includes single or plural agents and is considered equivalent to the phrase "comprising at least one agent." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless otherwise noted, technical terms are used according to conventional usage. Suitable methods and materials for the practice and/or testing of embodiments are described below. Such methods and materials are illustrative only and are not intended to be limiting. Other methods and materials similar or equivalent to those described herein can be used. For example, conventional methods well known in the art to which a disclosed invention pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

Additional terms commonly used in molecular genetics can be found in Benjamin Lewin, Genes V published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

All sequences associated with the GenBank® Accession Nos. mentioned herein are incorporated by reference in their entirety as were present on Jun. 23, 2010 to the extent permissible by applicable rules and/or law.

In order to facilitate review of the various embodiments of the disclosure, the following explanations of specific terms are provided:

Administration: To provide or give a subject an agent, such as an NRG-1 agonist or antagonist, by any effective route. Exemplary routes of administration include, but are not limited to, topical, injection (such as subcutaneous, intramuscular, intradermal, intraperitoneal, and intravenous), oral, sublingual, rectal, transdermal, intranasal, vaginal and inhalation routes.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional agent (such as an antineoplastic agent, such as Etoposide, Doxorubicin, methotrexate, and Vincristine) induces the desired response (such as inducing a therapeutic or prophylactic effect when administered to a subject). In an example, an agent includes a NRG-1 agonist or NRG-1 inhibitor (antagonist). In a particular example, an agent specifically modulates skin pigmentation, such as increases (e.g., an NRG-1 agonist) or decreases (e.g., NRG-1 inhibitor) pigmentation. In one example, an agent is an NRG-1 fragment that retains biological activity, such as modulating (e.g., increasing or decreasing) melanocyte proliferation or pigmentation, including but not limited to capable of activating ERBB receptors. In one example, the NRG variants are fragments of NRG-1 that include at least a portion of an extracellular domain of NRG-1 (e.g., amino acids 20-242 of human Type I NRG-1 of UniProtKB/Swiss-Prot Q02297 as available on Jun. 23, 2010 which is hereby incorporated by reference in its entirety) containing the receptor-binding EGF-like domain (e.g., amino acids 178-222 of human Type NRG-1 of UniProtKB/Swiss-Prot Q02297 as available on Jun. 23, 2010 which is hereby incorporated by reference in its entirety).

In other examples, an NRG-1 inhibitor is an ERBB inhibitor, such as a commercially available pan ERBB inhibitor, including, but not limited to Compound 39 (EGFR/ERBB2/ERBB4 inhibitor; Calbiochem, La Jolla, Calif.), CI-1033 (EGFR/ERBB2/ERBB4 inhibitor; Selleck Chemicals LLC, Houston, Tex.), PF-00299804 (EGFR/ERBB2/ERBB4 inhibitor, Pfizer, NY, N.Y.), PD168393 (Calbiochem, La Jolla, Calif.) or PD158780 (Calbiochem, La Jolla, Calif.).

Antibody: A polypeptide ligand comprising at least a light chain or heavy chain immunoglobulin variable region which specifically recognizes and binds an epitope of an antigen, such as NRG-1. In some examples, an NGR-1 antibody can act as an agonist or antagonist of NRG-1. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds mesothelin or NRG-1.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antisense compound: Refers to an oligomeric compound that is at least partially complementary to the region of a target nucleic acid molecule (such as an NRG-1 gene product) to which it hybridizes. As used herein, an antisense compound that is "specific for" a target nucleic acid molecule is one which specifically hybridizes with and modulates expression of the target nucleic acid molecule. As used herein, a "target" nucleic acid is a nucleic acid molecule to which an antisense compound is designed to specifically hybridize and modulate expression.

Nonlimiting examples of antisense compounds include primers, probes, antisense oligonucleotides, siRNAs, miRNAs, shRNAs and ribozymes. As such, these compounds can be introduced as single-stranded, double-stranded, circular, branched or hairpin compounds and can contain structural elements such as internal or terminal bulges or loops. Double-stranded antisense compounds can be two strands hybridized to form double-stranded compounds or a single strand with sufficient self complementarity to allow for hybridization and formation of a fully or partially double-stranded compound. In particular examples herein, the antisense compound is an antisense oligonucleotide, siRNA or ribozyme. An "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target RNA molecule, the duplex is recognized by RNase H (an enzyme that recognizes DNA:RNA duplexes), resulting in cleavage of the RNA.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

In one example, an agent that modulates NRG-1 activity is administered to a subject to prevent or treat skin cancer. "Skin cancer" is a malignant growth on the skin which can have many causes. Skin cancer generally develops in the epidermis (the outermost layer of skin), so a tumor is usually clearly visible. This makes most nonmelanoma skin cancers detectable in the early stages. The most common type of skin cancer is nonmelanoma skin cancer. Nonmelanoma skin cancers include all skin cancers except malignant melanoma (cancer that develop from melanocytes, the pigment-producing cells of the skin). There are many types of nonmelanoma skin cancers. Two common types of nonmelanoma skin cancer are basal cell carcinoma and squamous cell carcinoma. These two types of skin cancer are also known as keratinocyte carcinomas.

Basal cell carcinoma begins in the lowest layer of the epidermis, called the basal cell layer. About 70% to 80% of all skin cancers in men and 80% to 90% in women are basal cell carcinomas. They usually develop on sun-exposed areas, especially the head and neck. Basal cell carcinoma is slow growing. It is highly unusual for a basal cell cancer to spread to lymph nodes or to distant parts of the body. However, if a basal cell cancer is left untreated, it can grow into nearby areas and invade the bone or other tissues beneath the skin. After treatment, basal cell carcinoma can recur in the same place on the skin. Also, new basal cell cancers can start elsewhere on the skin. Within 5 years of being diagnosed with one basal cell cancer, 35% to 50% of people develop a new skin cancer.

Squamous cell carcinomas account for about 10% to 30% of all skin cancers. They commonly appear on sun-exposed areas of the body such as the face, ear, neck, lip, and back of the hands. Squamous cell carcinomas can also develop in scars or skin ulcers elsewhere. These carcinomas are generally more aggressive than basal cell cancers. Squamous cell carcinomas can sometimes start in actinic keratoses. Squamous cell carcinoma in situ (also called Bowen disease) is the earliest form of squamous cell skin cancer and involves cells that are within the epidermis and have not invaded the dermis.

Less common types of nonmelanoma skin cancer include Kaposi sarcoma, cutaneous lymphoma, skin adnexal tumors and various types of sarcomas and Merkel cell carcinoma. Together, these types of nonmelanoma skin cancer account for less than 1% of nonmelanoma skin cancers.

The most lethal type of skin cancer is melanoma. Melanoma (also known as malignant melanoma or cutaneous melanoma) is a cancer that begins in the melanocytes. Because most melanoma cells still produce melanin, melanoma tumors are usually brown or black. This form of skin cancer can be fatal if not treated early. In certain examples, a NRG-1 modulator is administered at a therapeutic effective concentration to prevent or inhibit one or more symptoms associated with melanoma.

Contacting: Placement in direct physical association, including both a solid and liquid form. Contacting can occur in vitro, for example, with isolated cells, such as a melanocyte, or in vivo by administering to a subject.

Control: A reference standard. A control can be a known value indicative of basal expression of a gene for example the amount (or average or range) of NRG-1 expressed in a melanocyte in a subject (such as a human) or a plurality of subjects that do not have skin cancer or a predisposition for developing skin cancer or some other skin disorder. A difference between the expression in a test sample (such as a biological sample obtained from a subject) and a control can be an increase or conversely a decrease. The difference can be a qualitative difference or a quantitative difference, for example a statistically significant difference.

In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Decrease: To reduce the quality, amount, or strength of something. In one example, an agent decreases the activity or expression of NRG-1, for example relative to no administration of the agent. In a particular example, an agent decreases the activity or expression of NRG-1 by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. In some examples, an agent decreases skin pigmentation, proliferation or combination thereof by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such decreases can be measured using the methods disclosed herein.

Effective amount: An amount of agent that is sufficient to generate a desired response, such as reducing or inhibiting one or more signs or symptoms associated with a condition or disease. When administered to a subject, a dosage will generally be used that will achieve target tissue concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example a chemotherapeutic agent), induces the desired response such as to prevent advancement, delay progression, or to cause regression of a skin cancer.

In one example, a desired response is to reduce or inhibit one or more symptoms associated with skin cancer, such as a melanoma. The one or more symptoms do not have to be completely eliminated for the composition to be effective. For example, an effective amount can be an amount decreases a sign or symptom by a desired amount, for example by at least 20%, at least 50%, at least 80%, at least 90%, at least 95%, at least 98%, or even at least 100%, as compared to the sign or symptom in the absence of the NRG-1 modulator. In one particular example, a desired response is to reduce or inhibit the activity of NRG-1 by a desired amount, for example by at least 20%, at least 50%, at least 60%, at least 70%, at least 80%, at least 90%, at least 95%, at least 98%, or even at least 100%, as compared to the activity and/or expression in the absence of the NRG-1 modulator.

The effective amount of an agent that includes one of the disclosed therapeutic agents (such as NRG-1 modulators), that is administered to a human or veterinary subject will vary depending upon a number of factors associated with that subject, for example the overall health of the subject. An effective amount of an agent can be determined by varying the dosage of the product and measuring the resulting therapeutic response, such as the regression of a melanoma. Effective amounts also can be determined through various in vitro, in vivo or in situ immunoassays. The disclosed agents can be administered in a single dose, or in several doses, as needed to obtain the desired response. However, the effective amount of can be dependent on the source applied, the subject being treated, the severity and type of the condition being treated, and the manner of administration.

Generally a suitable dose of a peptide, such as an NRG-1 peptide fragment, is about 1 milligram per kilogram (mg/kg) to about 50 mg/kg, such as a dose of about 1 mg/kg, about 2 mg/kg, about 5 mg/kg, or about 20 mg/kg administered parenterally. For example, a suitable dose is about 1 mg/kg to about 100 mg/kg, such as a dose of about 1 mg/kg, about 10 mg/kg, about 20 mg/kg, about 50 mg/kg, or about 100 mg/kg administered orally. Unit dosage forms are also possible, for example 50 mg, 100 mg, 150 mg or 200 mg, or up to 400 mg per dose. However, other higher or lower dosages also could be used, such as from about 0.001 mg/kg to about 1 g/kg, such as about 0.1 to about 500 mg/kg, including about 0.5 mg/kg to about 200 mg/kg. In particular examples, an effective dose of an agent including a disclosed NRG-1 polypeptide is at least 1 µg daily (such as 1-100 µg or 5-50 µg) if administered via injection, or at least 1 mg daily if administered topically (such as 1-100 mg or 5-50 mg). In one example, an effective dose is between 1 ng/ml to 500 ng/ml, such as between 20 ng/ml to 100 ng/ml, including about 10 ng/ml, about 20 ng/ml, about 30 ng/ml, about 40 ng/ml, about 50 ng/ml, about 60 ng/ml, about 70 ng/ml, about 80 ng/ml, about 90 ng/ml or about 100 ng/ml administered in topical solution. In particular examples, such daily dosages are administered in one or more divided doses (such as 2, 3, or 4 doses) or in a single formulation. The disclosed agents can be administered alone, in the presence of a pharmaceutically acceptable carrier, in the presence of other therapeutic agents (such as other anti-neoplastic agents), cosmetic agents, or both.

Epidermal growth factor receptor (EGFR) family: A family of protein tyrosine kinases (PTKs), also known as the ERBB family. The ERBB PTK family includes four receptor kinases, ERBB1 (EGFR1, HER1), ERBB2 (c-Neu, HER2), ERBB3 (HER3) and ERBB4 (HER4). The ERBB kinases regulate a wide range of cellular responses, including cell proliferation, survival, migration and differentiation. ERBB signaling pathways are known to be altered in a wide variety of cancers.

Increase: To enhance the quality, amount, or strength of something. In one example, an agent increases the activity or expression of NRG-1, for example relative to an absence of the agent. In a particular example, an agent increases the activity or expression of NRG-1 by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. In some examples, an agent increases skin pigmentation or melanocyte proliferation by at least 10%, at least 20%, at least 50%, or even at least 90%, including between 10% to 95%, 20% to 80%, 30% to 70%, 40% to 50%, such as 10%, 20%, 30%, 40%, 50%, 60%, 70%, 80%, 85%, 90%, 95%, 98%, or 100%. Such increases can be measured using the methods disclosed herein.

Incubating: A term that includes a sufficient amount of time for an agent to interact with a cell or tissue.

Inhibitor: Any chemical compound, nucleic acid molecule, peptide or polypeptide such as an antibody or antisense compound that can reduce activity or expression of a gene product or interfere with expression of a gene (such as NRG-1), respectively. In some examples, an inhibitor can reduce or inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. In some examples, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization. In one example, an inhibitor is an NRG-inhibitor (such as an inhibitory RNA or inhibitory antibody used to inhibit NRG-1 activity or expression). NRG-family inhibitors are known in the art and include, but are not limited to ERBB inhibitors.

An ERBB2, ERBB3 or ERBB4 inhibitor refers to any molecule that inhibits expression or activity of ERBB2, ERBB3, or ERBB4, respectively, such as kinase activity of ERBB2, ERBB3 or ERBB4. Inhibitor compounds include, but are not limited to, small molecules, polypeptides and nucleic acid molecules (such as antisense compounds). In some embodiments, an ERBB2, ERBB3 or ERBB4 inhibitor is a broad-spectrum inhibitor that inhibits activity of multiple members of the EGFR family, such as a commercially available pan ERBB inhibitor, including, but not limited to Compound 39 (EGFR/ERBB2/ERBB4 inhibitor; Calbiochem, La Jolla, Calif.), CI-1033 (EGFR/ERBB2/ERBB4 inhibitor; Selleck Chemicals LLC, Houston, Tex.), PF-00299804 (EGFR/ERBB2/ERBB4 inhibitor, Pfizer, NY, N.Y.), PD168393 (Calbiochem, La Jolla, Calif.) or PD158780 (Calbiochem, La Jolla, Calif.). EGFR family inhibitors are known in the art (see, for example, PCT Publication Nos. WO 2008/005983, WO 03/012072 and WO 03/070912; and U.S. Patent Application Publication Nos. 2006/0233808 and 2006/0128636). In some embodiments, an ERBB2, ERBB3 or ERBB4 inhibitor selectively inhibits expression or activity of ERBB2, ERBB3 or ERBB4, respectively, and not other EGFR family members (see, for example, U.S. Pat. No. 5,811,098). In some embodiments, the ERBB2, ERBB3, or ERBB4 inhibitor is a kinase inhibitor. Kinase inhibitors are well known in the art (see, for example, U.S. Patent Application Publication Nos. 2008/0031893; 2006/0148824; and 2002/0156083). In particular examples, the ERBB4 inhibitor is lapatinib (Burris et al., *J. Clin. Oncol.* 23(23):5305-5313, 2005).

Modulate or modulating: To adjust, alter, regulate an activity, a degree or rate of such including an increase or a decrease in biological activity of a molecule. In one example, a NRG-1 modulator is administered to modulate, either increase (NRG-1 agonist) or decrease (NRG-1 inhibitor) NRG-1 activity or expression.

Neuregulins (NRGs): A family of four structurally-related proteins (NRG-1, NRG-2, NRG-3, and NRG-4) that are part of the epidermal growth factor family of proteins. These proteins have been shown to have diverse functions in the development of the nervous system. The basic structure of NRG-1 includes a N-terminal region, an immunoglobulin (Ig) motif, a glycosylation-rich spacer domain, an EGF-like domain, and a cytoplasmic tail. NRG-1 has several different isoforms including the following isoforms stemming from alternative splicing: Type I NRG-1 (also known as Heregulin (HRGβ1), NEU differentiation factor (NDF), or acetylcholine receptor inducing activity (ARIA)); Type II NRG-1 (also known as Glial Growth Factor-2 (GGF2)); Type III NRG-1 (also known as sensory and motor neuron-derived factor (SMDF)); Type IV NRG-1; Type V NRG-1; and Type VI NRG-1. They are tissue-specifically expressed and differ significantly in their structure. Type I NRG-1 isoforms all contain immunoglobulin (Ig) and epidermal growth factor-like (EGF-like) domains. Type II isoforms contain a kringle-like sequence plus Ig and EGF-like domains; and the Type III isoform shares only the EGF-like domain with other isoforms. The receptors for all NRG-1 isoforms are the ERBB family of tyrosine kinase transmembrane receptors. Through interaction with ERBB receptors, NRG-1 isoforms induce the growth and differentiation of epithelial, neuronal, glial, and other types of cells.

NRG-1 sequences are publicly available. For example, GenBank Accession numbers NM_013956, NM_013957, NM_013958, NM_013964, and NM_004495 disclose Type I NRG-1 mRNA sequences. GenBank Accession number NM_013962 discloses a human Type II NRG-1 mRNA sequence. GenBank Accession number NM_013959 discloses human Type III NRG-1 mRNA sequence, respectively. In one particular example, an exemplary Type I NRG-1 mRNA sequence has the nucleic acid sequence SEQ ID NO: 8 (GenBank Accession No. NM_013956 which is hereby incorporated by reference in its entirety). Nucleic acids 1085-1180 encode the EGF domain (amino acids 190-221) provided in SEQ ID NO: 7.

Human NRG-1 amino acid sequences have been deposited with GenBank (see for example, GenBank Accession Numbers NP_001153467.1, NP_001153468.1, NP_001153471.1, NP_001153473.1, NP_001153474.1, NP_001153476.1, NP_001153477.1, NP_001153479.1, NP_001153480.1, NP_004486.2, NP_039250.2, NP_039251.2, NP_039252.2, NP_039253.1, NP_039254.1, NP_039255.1, NP_039256.2, NP_039258.1 for human Type I NRG-1) as well as other depositories (such as UniProtKB/Swiss-Prot Q02297, A5YAK4, A5YAK5, O14667, P98202, Q02298, Q02299, Q07110, Q07111, Q12779, Q12780, Q12781, Q12782, Q12783, Q12784, Q15491, Q7RTV9, Q7RTW0, Q7RTW1, Q7RTW2, Q8NFN1, Q8NFN2, Q8NFN3, and Q9UPE3) and are publicly accessible. In one particular example, an exemplary NRG-1 amino acid sequence has the following amino acid sequence:
mserkegrgkgkgkkkergsgkkpe-
saagsqspalppqlkemksqesaagsklylrcetsseysslrfkwfkngn eln-
rknkpqnikiqkkpgksel-
rinkasladsgeymckvisklgndsasanitivesneiitgmpastegayvsses
pirisystegantsssststtg
tshlvkcaekektfcvnggecfmvkdl
snpsrylckcpneftgdrcnyvmasnykhlgiefineaeelyqkryltitgiciallvvgimcvvaycktkkqrkklhdrlrqslrsernnmmniangphhpnppp envqlvnqyvsknvissehivereaets-fstshytstahhsttvtqtpshswsnghtesilseshsvivmssvensrhs sptgg-prgrlngtggprecnsflrharetp-dsyrdsphseryvsamttparmspvdfhtpsspksppsemsppvss mtvsmpsmayspfineeerplllvtp-prlrekkfdhhpqqfssfhhnpandsnslpasplrivedeeyettqeyepa qepvkklansrrakrtkpnghian-flevdsntssqssnsesetedervgedtpflgiqnplaasleatpafrladsrtnpa grfstqeeiqarlssvianqdpiav (SEQ ID NO: 7); a biologically active portion of the protein spanning from amino acid 176-246 (as double underlined) and the EGF domain within such fragment (as single underlined, amino acids 190-221).

Further, NRG-1 sequences from other species also are publicly available, such as mouse NRG-1. GenBank Accession numbers XM_620542 and XP_620642 disclose murine Type I NRG-1 mRNA and protein sequences, respectively. One skilled in the art will appreciate that NRG nucleic acid and protein molecules can vary from those publicly available, such as those having one or more substitutions, deletions, insertions, or combinations thereof, while still retaining NRG biological activity. In some embodiments, the NRG variants that retain biological activity are conservative variants of NRG-1, such as conservative variants of NRG-1 with at least 80%, at least 85%, at least 90%, at least 95%, at least 98%, such as 81%, 82%, 83%, 84%, 85%, 86%, 87%, 88%, 89%, 90%, 91%, 92%, 93%, 94%, 95%, 96%, 97%, 98%, or 99% sequence identity to human NRG-1 (e.g., human Type I NRG-1 mRNA or protein) such as human NRG-1 with a sequence set forth by any of the disclosed GenBank or UniProtKB/Swiss-Prot Accession Numbers and/or SEQ ID NO: 7. In other embodiments, the NRG variants are fragments of NRG that retain biological activity, such as modulating (e.g., increasing or decreasing) melanocyte proliferation or pigmentation, including but not limited to capable of activating ERBB receptors. In one example, the NRG fragments of NRG-1 include at least a portion of the extracellular domain of NRG-1 (e.g., amino acids 20-242 of human Type I NRG-1 of UniProtKB/Swiss-Prot Q02297) containing the receptor-binding EGF-like domain (e.g., amino acids 178-222 of human Type NRG-1 of UniProtKB/Swiss-Prot Q02297). In some examples, the NRG-1 fragments include a portion of SEQ ID NO: 7, such as amino acids 176-246 or amino acids 190-221.

In some examples, the NRG-1 fragments include a EGF-domain of NRG-1 set forth as SEQ ID NOs: 9-11 or fragment of such sequences, including, but not limited to, an 8-mer (such as an 8-mer NGR-1 peptide including amino acids 3-10 of SEQ ID NO: 10, amino acids 8-15 of SEQ ID NO: 10, amino acids 12-19 of SEQ ID NO: 10, amino acids 16-23 of SEQ ID NO: 10, amino acids 20-27 of SEQ ID NO: 10) or 16-mer (such as a 16-mer NRG-1 peptide including amino acids 1-16 of SEQ ID NO: 9 or SEQ ID NO: 10, .a 16-mer NRG-1 peptide including amino acids 17-32 of SEQ ID NO: 9, a 16-mer NRG-1 peptide including amino acids 8-23 of SEQ ID NO: 9 or a 16-mer NRG-1 peptide including amino acids 17-32 of SEQ ID NO: 10).

Methods of determining whether NRG variants or fragments are capable of modulating melanocyte proliferation or pigmentation are known in the art, including commercially available cell proliferation assays, use of commercially available melanin, and are described herein (e.g., the Examples).

Peptide, Polypeptide, and/or Protein: Any compound composed of amino acids, amino acid analogs, chemically bound together. Amino acids generally are chemically bound together via amide linkages (CONH). Additionally, amino acids may be bound together by other chemical bonds. For example, the amino acids may be bound by amine linkages. Peptides include oligomers of amino acids, amino acid analog, or small and large peptides, including polypeptides or proteins. In some examples, a peptide is NRG-1 peptide, such as a peptide that retains NRG-1 biological activity, such as activity to modulate ERBB4 (e.g., includes amino acids 176-246 corresponding to the extracellular domain of native NRG-1).

"Peptide" applies to amino acid polymers to naturally occurring amino acid polymers and non-naturally occurring amino acid polymer as well as in which one or more amino acid residue is a non-natural amino acid, for example a artificial chemical mimetic of a corresponding naturally occurring amino acid.

A "polypeptide" is a polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

The term "soluble" refers to a form of a polypeptide that is not inserted into a cell membrane.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine. In some examples, one or more conservative amino acid substitutions are made to a NRG-1 peptide disclosed herein while maintaining the biological activity of native NRG-1 (such as modulating ERBB activity, including ERBB2, ERBB3 and/or ERBB4 activity).

Pharmaceutical composition: A chemical compound or composition capable of inducing a desired therapeutic or prophylactic effect when properly administered to a subject. A pharmaceutical composition can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical composition includes a therapeutically effective amount of at least one NRG-1 modulatory agent.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 19th Edition (1995), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pigment or Pigmentation: Any colored material of plant or animal cells. Many biological structures, such as skin, eyes, fur and hair contain pigments (such as melanin) in specialized cells called chromatophores. Melanin is the primary determinant of skin color. Methods of measuring melanocyte pigmentation levels are known in the art, such as melanin content assays, and are described herein (e.g., the Examples).

Preventing a disease: "Preventing" a disease (such as metastatic melanoma) refers to inhibiting the full development of a disease.

Proliferation: The continuous development of cells in tissue formation and cell formation. Methods of measuring melanocyte proliferation are known in the art, including commercially available cell proliferation assay kits (such as CyQUANT® cell proliferation assays from Invitrogen (Carlsbad, Calif.)) and are described herein (e.g., the Examples).

RNA interference (RNAi): Refers to a cellular process that inhibits expression of genes, including cellular and viral genes. RNAi is a form of antisense-mediated gene silencing involving the introduction of double stranded RNA-like oligonucleotides leading to the sequence-specific reduction of RNA transcripts. Double-stranded RNA molecules that inhibit gene expression through the RNAi pathway include siRNAs, miRNAs, and shRNAs. A short interfering RNA (siRNA) is a double stranded nucleic acid molecule capable of RNA interference or "RNAi." (See, for example, Bass *Nature* 411: 428-429, 2001; Elbashir et al., *Nature* 411: 494-498, 2001; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.) As used herein, siRNA molecules need not be limited to those molecules containing only RNA, but further encompasses chemically modified nucleotides and non-nucleotides having RNAi capacity or activity. In an example, a siRNA molecule is one that reduces or inhibits the biological activity or expression of NRG-1, such as those that are commercially available from, but not limited to, Sigma Aldrich (St. Louis, Mo.) or Applied Biosystems (Foster City, Calif.). In one example, a shRNA is a sequence of RNA that makes a tight hairpin turn and can be used to silence gene expression via the RNAi pathway. The shRNA hairpin structure is cleaved by the cellular machinery into siRNA. In one example, the shRNA is an NRG-1 shRNA (such as a commercially available NRG-1 shRNG from Sigma Aldrich, St. Louis, Mo.).

Sample: A biological specimen containing genomic DNA, RNA, protein, or combinations thereof, obtained from a subject. Examples include, but are not limited to, peripheral blood, urine, saliva, tissue biopsy (such as skin tissue), surgical specimen, and autopsy material. In one example, a sample includes a biopsy of a melanoma tumor or a sample of normal tissue (from a subject not afflicted with a known disease or disorder, such as a cancer-free subject).

Subject or patient: A term that includes human and non-human mammals, such as those having skin cancer or those at risk for developing skin cancer. In one example, the subject or patient is a mammal, such as a human. In another example, a subject does not include a mouse. "Patient" and "subject" are used interchangeably herein.

Substitution: With reference to an amino acid in a polypeptide "substitution" means replacement of one amino acid with a different amino acid.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for detecting a skin disorder, such as skin cancer. In one example, reducing or inhibiting one or more symptoms or signs associated with a skin disorder, includes modulating the activity of NRG-1 by a desired amount, for example by at least 20%, at least 50%, at least 60%, at least 70%, at least 80%, at least 90%, at least 95%, at least 98%, or even at least 100%, as compared to the activity and/or expression in the absence of the NRG-1 modulatory agent.

Therapeutic: A generic term that includes both diagnosis and treatment. Therapeutic agent is a chemical compound, small molecule, or other composition, such as an antisense compound, antibody, peptide, nucleic acid molecule, protease inhibitor, hormone, chemokine or cytokine, capable of inducing a desired therapeutic or prophylactic effect when properly administered to a subject. For example, therapeutic agents for melanoma include agents that prevent or inhibit development or metastasis of melanoma.

Treating: A term when used to refer to the treatment of a cell or tissue with an agent, such as a therapeutic agent, includes contacting or incubating an agent with the cell or tissue. A treated cell is a cell that has been contacted with a desired composition in an amount and under conditions sufficient for the desired response. In one example, a treated cell is a cell that has been exposed to a composition including an agent with NRG-1 modulatory activity under conditions sufficient for a sign or symptoms associated with a skin disorder to be suppressed.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "noncancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "normal cell" is a non-diseased cell, such as non-tumor cell, non-malignant, uninfected cell, such as normal melanocytes. In some examples, the disclosed compositions and methods are used to modulate proliferation and/or pigmentation in a normal melanocyte, such as for cosmetic purposes (including lightening or darkening skin color) or to prevent or inhibit UV skin damage. A "cancer-free" subject has not been diagnosed with a cancer of that organ and does not have detectable cancer.

Under conditions sufficient for: A phrase that is used to describe any environment that permits the desired activity. In one example, "under conditions sufficient for" includes administering an agent that modulates NRG-1 activity to a subject sufficient to allow the agent to have the desired activity. In particular examples, the desired activity is altering the activity (such as the expression) of NRG-1 thereby modulating pigmentation, proliferation or a combination thereof of the melanocyte.

Untreated cell: A cell that has not been contacted with a desired agent, such as an agent with NRG-1 modulatory activity. In an example, an untreated cell is a cell that receives the vehicle in which the desired agent was delivered.

III. Compositions

Disclosed herein are compositions for use to treat a skin disorder (such as skin cancer or undesired dark skin pigmentation) or for cosmetic purposes (such as to alter skin color). A disclosed composition includes an agent that is an NRG-1 modulatory agent, such as an NRG-1 agonist or NRG-1 inhibitor/antagonist. In a particular example, an agent specifically modulates skin pigmentation or proliferation, such as increases (e.g., an NRG-1 agonist) or decreases (e.g., NRG-1 inhibitor) melanocyte proliferation or pigmentation. In some examples, NRG-1 agonists are used for prophylactic purposes, such as to prevent UV skin damage (e.g., a sunscreen) or for cosmetic purposes such as to alter skin color, such as to darken skin color (e.g., a self-tanning lotion). In some examples, NRG-1 inhibitors are used to treat skin disorders associated with hyperpigmentation or skin cancer, including melanoma. NRG-1 inhibitors can also be used to for cosmetic purposes such as to alter skin color, such as to lighten skin color.

i. NRG-Agonists

An NRG-1 agonist is an agent that increases or retains NRG-1 biological activity, such as increasing melanocyte proliferation or pigmentation, including but not limited to capable of activating ERBB receptors. Methods of measuring such activating are known in the art and disclosed herein. Exemplary NRG-1 agonists include NRG-1 antibodies and native or variant NRG-1 peptides (such as a fragment thereof) that retains biological activity. Disclosed NRG-1 peptides maintain the ability to increase NRG-1 expression or biological activity, such as the ability to increase melanocyte proliferation, pigmentation or a combination thereof. In some example, a disclosed NRG-1 peptide includes at least a portion of the extracellular domain of NRG-1 (e.g., amino acids 20-242 of human Type I NRG-1 of UniProtKB/Swiss-Prot Q02297 as available on Jun. 23, 2010 which is hereby incorporated by reference in its entirety) or amino acids containing the receptor-binding EGF-like domain (e.g., amino acids 178-222 of human Type NRG-1 of UniProtKB/Swiss-Prot Q02297 as available on Jun. 23, 2010 which is hereby incorporated by reference in its entirety) and maintain the ability to be increase NRG-1 activity, such as NRG-1 expression or biological activity (e.g., activating ERBB4).

In a particular example, a NRG-1 peptide variant is disclosed which has at least 80%, at least 90%, at least 95%, at least 98%, such as 80%, 82%, 85%, 90%, 93%, 98% or 100% sequence identity with an amino acid sequence set forth by SEQ ID NO: 7.

In some examples, NRG-1 peptides are about 4 to 8, such as 5 to 7, amino acids in length to about 250 amino acids in length, such as between 10 to 40 amino acids in length, including 10 to 25 amino acid residues in length, and maybe at least 4, 5, 6, 7, 8, 9, 10 or 11 residues in length, for example 5-15 residues, 10-50 residues, or 10-30 residues, for example this many contiguous resides of SEQ ID NO: 7. The NRG-1 peptides in some examples are about or no more than about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, or about 250 amino acids in length, for example about 40 to about 69, about 46 to about 92, about 69 to about 115, about 92 to about 138, about 115 to about 161, about 138 to about 184, about 161 to about 207, about 184 to about 230 amino acids or about 207 to 250 amino acids in length or greater, for example this many contiguous resides of SEQ ID NO: 7. In this context, it is understood that "about" refers to an integer quantity. In some examples, the NRG-1 peptide is even greater than 250 amino acids in length, for example when including more than the extracellular domain of native NRG-1 or part of a larger fusion protein.

In some examples, the NRG-1 peptide includes about 4 to 8, such as 5 to 7, amino acids to about 70 amino acids and includes at least a portion of SEQ ID NO: 7 corresponding to amino acids 176-246 (such as one or more amino acids corresponding to amino acids 190-221 of SEQ ID NO: 7), such as between 10 to 70 amino acids and even at least 4, 5, 6, 7, 8, 9, 10 or 11 residues in length, for example 5-15 residues, 10-50 residues, or 10-30 residues for example this many contiguous resides of SEQ ID NO: 7. The NRG-1 peptides in some examples are about or no more than about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, or about 70 amino acids in length. In this context, it is understood that "about" refers to an integer quantity. In this context, it is understood that "about" refers to an integer quantity. These lengths in some examples are numbers of contiguous amino acids of SEQ ID NO: 7.

In some examples, the NRG-1 fragments include or consist of an EGF-domain of NRG-1 set forth as SEQ ID NOs: 9-11 or fragment of such sequences, including, but not limited to, an 8-mer (such as an 8-mer NGR-1 peptide including amino acids 3-10 of SEQ ID NO: 10, amino acids 8-15 of SEQ ID NO: 10, amino acids 12-19 of SEQ ID NO: 10, amino acids 16-23 of SEQ ID NO: 10, amino acids 20-27 of SEQ ID NO: 10) or 16-mer (such as a 16-mer NRG-1 peptide including amino acids 1-16 of SEQ ID NO: 9 or SEQ ID NO: 10, .a 16-mer NRG-1 peptide including amino acids 17-32 of SEQ ID NO: 9, a 16-mer NRG-1 peptide including amino acids 8-23 of SEQ ID NO: 9 or a 16-mer NRG-1 peptide including amino acids 17-32 of SEQ ID NO: 10).

The disclosed NRG-1 peptides can be joined to a non-NRG-1 peptide linker, such a linker between two and ten amino acids in length, such as about 2, about 3, about 4, about 5, about 6, about 7, about 8, about 9 or about 10 amino acids in length. Depending on such factors as the molecules to be linked, and the conditions in which the peptide is being administered (such as if the peptide is being used in a method of detection), the linker can vary in length and composition for optimizing such properties as flexibility, and stability. The linker is a peptide heterologous to the NRG-1. In some examples, a linker is peptide such as poly-lysine, poly-glutamine, poly-glycine, poly-proline or any combination combinations thereof. In some examples, the peptide linker can be designed to be either hydrophilic or hydrophobic in order to enhance the desired binding characteristics of NRG-1 and ERBB2, ERBB3, and/or ERBB4, thereby enhancing the activity of NRG-1. The peptide linker and the individual units of the NRG-1 can be encoded as a single fusion polypeptide such that the peptide linker and the individual units of the NRG-1 are joined by peptide bonds.

NRG-1 peptides can be identified by methods known to those of ordinary skill in the art, including those disclosed in *Exp. Cell Res.* 259:54-63 (2000), which is hereby incorporated by reference in its entirety. For example, NRG-1 peptides can be synthesized in various lengths, such as overlapping 15-mers of the entire active fragment of SEQ ID NO: 7 (amino acid residues 176-246), and their activity to increase pigmentation or proliferation of melanocytes can be determined in a functional assay, including those known to ordinary skill in the art and as provided herein (see Examples). Functional activity of the disclosed peptides can also be determined or confirmed in a MelanoDerm human skin model (Id.). A minimal size of NRG-1 peptide can be determined by similar studies in which smaller and smaller peptides in the bioactive region(s) are synthesized and evaluated until a minimal length is determined.

The present disclosure contemplates further modifications of a NRG-1 peptide composition that do not affect the ability of the peptide to reduce or inhibit one or more symptoms associated with a skin disorder. Such modifications include amino acid substitutions, insertions or deletions, and modifications, for example, to reduce antigenicity of the peptide, to enhance the stability of the conjugate and/or to improve the pharmacokinetics of the conjugate. In one example, further modifications result in a polypeptide that differs by only a small number of amino acids. Such modifications include insertions (for example, of 1-3 or more residues), or substitutions that do not interfere with the ability of the peptide to selectively modulate the effects of NRG-1 on melanocytes.

Various modifications to reduce immunogenicity and/or improve the half-life of therapeutic proteins are known in the art. For example, the peptides can undergo glycosylation, isomerization, or deglycosylation according to standard methods known in the art. Similarly, the peptides can be modified by non-naturally occurring covalent modification for example by addition of polyethylene glycol moieties (pegylation) or lipidation. In one example, the compositions are conjugated to polyethylene glycol (PEGylated) to improve their pharmacokinetic profiles. Conjugation can be carried out by techniques known to those skilled in the art (see, for example, Deckert et al., *Int. J. Cancer* 87: 382-390, 2000; Knight et al., *Platelets* 15: 409-418, 2004; Leong et al., *Cytokine* 16: 106-119, 2001; and Yang et al., *Protein Eng.* 16: 761-770, 2003). In one example, antigenic epitopes can be identified and altered by mutagenesis. Methods of identifying antigenic epitopes are known in the art (see for example, Sette et al., *Biologicals* 29:271-276, 2001), as are methods of mutating such antigenic epitopes. In one example, modifications are incorporated to decrease the toxicity of the peptide. The general toxicity of the peptides according to the present disclosure can be tested according to methods known in the art. For example, the overall systemic toxicity of a disclosed peptide can be tested by determining the dose that kills 100% of melanocytes (i.e., LD100) following a single treatment.

Also disclosed herein are polynucleotides that encode polypeptides that have NRG-1 activity. A polynucleotide is a polymeric form of nucleotides of any length, either ribonucleotides or deoxynucleotides, and includes both double- and single-stranded DNA and RNA. A polynucleotide may include nucleotide sequences having different functions, including, for instance, coding sequences, and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. For example, a polynucleotide can be a portion of a vector, such as an expression or cloning vector, or a fragment.

The present disclosure also provides polynucleotides encoding a polypeptide of the present disclosure, such as, for example, a polypeptide having NRG-1 activity. A polynucleotide can include nucleotide sequences having different functions, including for instance coding sequences, and non-coding sequences such as regulatory sequences. "Coding sequence" and "coding region" are used interchangeably and refer to a polynucleotide that encodes a polypeptide and, when placed under the control of appropriate regulatory sequences expresses the encoded polypeptide. The boundaries of a coding region are generally determined by a translation start codon at its 5' end and a translation stop codon at its 3' end. A regulatory sequence is a nucleotide sequence that regulates expression of a coding region to which it is operably linked. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

Polynucleotides encoding a polypeptide of the disclosure can be obtained from an organism known to express NRG-1 peptides. Methods for isolating a polynucleotide encoding a polypeptide employs standard cloning techniques known to the art (see, for example, Sambrook et al., Molecular Cloning: A Laboratory Manual., Cold Spring Harbor Laboratory Press (1989) or Ausubel et al., (Eds.) Current Protocols in Molecular Biology, John Wiley & Sons, Inc. New York, N.Y. (1994)).

A polynucleotide encoding a NRG-1 polypeptide can be included in an expression vector to direct expression of the NRG-1 nucleic acid sequence. The term vector includes, but is not limited to, plasmid vectors, viral vectors, cosmid vectors, or artificial chromosome vectors. Typically, a vector is capable of replication in a bacterial host, for instance E. coli, or in a eukaryotic cell. In one embodiment, the vector is a plasmid vector. Selection of a vector depends upon a variety of desired characteristics in the resulting construct, such as a selection marker, vector replication rate, and the like. Suitable host cells for cloning or expressing the vectors herein are prokaryotic or eukaryotic cells.

Other expression control sequences including appropriate promoters, enhancers, transcription terminators, a start codon (i.e., ATG) in front of a protein-encoding gene, splicing signal for introns, maintenance of the correct reading frame of that gene to permit proper translation of mRNA, and stop codons can be included with a polynucleotide sequence in an expression vector. Generally expression control sequences include a promoter, a minimal sequence sufficient to direct transcription.

The expression vector typically contains an origin of replication and a promoter. In some instances, the expression vector comprises specific genes which allow phenotypic selection of the transformed cells (such as an antibiotic resistance cassette). Generally, the expression vector will include a promoter. The promoter can be inducible or constitutive. The promoter can be tissue specific. In one embodiment, the promoter is a heterologous promoter. In one example, the polynucleotide encoding the NRG-1 polypeptide is located downstream of the desired promoter. Optionally, an enhancer element is also included, and can generally be located anywhere on the vector and still have an enhancing effect. However, the amount of increased activity will generally diminish with distance.

An expression vector can optionally include a ribosome binding site (a Shine Dalgarno site for prokaryotic systems or a Kozak site for eukaryotic systems) and a start site to initiate translation of the transcribed message to produce the polypeptide. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, T1 and T2, are an often used terminator that is incorporated into bacterial expression systems. Transcription termination sequences in vectors for eukaryotic cells typically include a polyadenylation signal 3' of the coding region.

Also useful are expression vectors that provide for transient expression in eukaryotic cells of a coding sequence encoding a polypeptide disclosed herein. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, including a suitable expression vector and a host cell, allow for the convenient positive identification of polypeptides that are targeted to the appropriate organelle. Methods for the transient expression of coding regions are well known in the art.

Construction of vectors containing a polynucleotide of the disclosure employs standard ligation techniques well known in the art (see, for example, Sambrook et al., *Molecular Cloning: A Laboratory Manual.*, Cold Spring Harbor Laboratory Press (1989) or Ausubel et al., (Eds.) *Current Protocols in Molecular Biology*, John Wiley & Sons, Inc. New York, N.Y. (1994). Vectors suitable for use include, but are not limited to, pTYB2 (New England Biolabs; Garvish and Lloyd, *J. Mol. Biol.* 295:479-7488, 2000), pcDNA3.1 (Invitrogen, Carlsbad, Calif.) and pET-22b (Novagen).

Expression vectors including a polynucleotide encoding a NRG-1 polypeptide can be used to transform host cells. Hosts can include isolated microbial, yeast, insect and mammalian cells, as well as cells located in the organism, such as a human. Biologically functional viral and plasmid DNA vectors capable of expression and replication in a host are known in the art, and can be used to transfect any cell of interest.

ii. NRG-1 Inhibitors/Antagonists

Exemplary NRG-1 inhibitor/antagonists are known in the art and include, but are not limited to NRG-1 inhibitory antibodies, chemical compositions and NRG-1 antisense compounds that inhibit melanocyte proliferation or pigmentation.

NRG-1 family inhibitors include ERBB inhibitors, such as a commercially available pan ERBB inhibitor, including, but not limited to Compound 39 (EGFR/ERBB2/ERBB4 inhibitor; Calbiochem, La Jolla, Calif.), CI-1033 (EGFR/ERBB2/ERBB4 inhibitor; Selleck Chemicals LLC, Houston, Tex.), PF-00299804 (EGFR/ERBB2/ERBB4 inhibitor, Pfizer, NY, N.Y.), PD168393 (Calbiochem, La Jolla, Calif.) or PD158780 (Calbiochem, La Jolla, Calif.).

In some embodiments, NRG-1 antisense compounds include NRG-1 antisense compounds that hybridize to a NRG-1 nucleic acid sequence (such as to SEQ ID NO: 8) and effects the modulation of NRG-1 gene expression activity, or function, such as transcription, translation or splicing. In one example, a disclosed NRG-1 antisense compound targets a NRG-1 nucleic acid sequence (such as SEQ ID NO: 8) to alter the activity or function of the nucleic acids which encode the active domain of an NRG-1 protein (such as amino acids 176-246 of SEQ ID NO: 7) so that the resulting NRG-1 protein has reduced NRG-1 expression or activity, such as reduced ERBB activity.

Any type of antisense compound that specifically targets and regulates expression of NRG-1 is contemplated for use with the disclosed methods. Such antisense compounds include single-stranded compounds, such as antisense oligonucleotides, and double-stranded compounds, including compounds with at least partial double-stranded structure, including siRNAs, miRNAs, shRNAs and ribozymes. Methods of designing, preparing and using antisense compounds that specifically target NRG-1 gene are within the abilities of one of skill in the art. Furthermore, sequences for NRG-1 are publicly available and are disclosed herein.

Antisense compounds specifically targeting NRG-1 can be prepared by designing compounds that are complementary to a NRG-1 nucleotide sequence, particularly the mRNA sequence, such as that provided in SEQ ID NO: 8 or other publicly available NRG-1 mRNA sequences (such as GenBank Accession numbers NM_013956, NM_013957, NM_013958, NM_013964, and NM_004495 disclose Type I NRG-1 mRNA sequences; GenBank Accession number NM_013962, human Type II NRG-1 mRNA sequence; and GenBank Accession number NM_013959, human Type III NRG-1 mRNA sequence). Antisense compounds targeting the desired gene need not be 100% complementary to the gene to specifically hybridize and regulate expression the target gene. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Application Publication No. 2003-0228689).

In one non-limiting embodiment, double-stranded antisense compounds encompass siRNAs. siRNAs are double-stranded compounds having a first and second strand (referred to as the "sense strand" and "antisense strand"). In some embodiments, each strand has a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleotides to form an overhang. In one non-limiting example, the first strand of the siRNA is antisense to the target nucleic acid (the antisense strand), while the second strand is complementary to the first strand (the sense strand).

Once the antisense strand is designed to target a particular nucleic acid target, the sense strand of the NRG-1 siRNA can then be designed and synthesized as the complement of the antisense strand and either strand may contain modifications or additions to either terminus. For example, in one embodiment, both strands of the NRG-1 siRNA duplex are complementary over the central nucleotides, each having overhangs at one or both termini. It is possible for one end of a duplex to be blunt and the other to have overhanging nucleotides. In one embodiment, the number of overhanging nucleotides is from 1 to 6 on the 3' end of each strand of the duplex. In another embodiment, the number of overhanging nucleotides is from 1 to 6 on the 3' end of only one strand of the duplex. In a further embodiment, the number of overhanging nucleotides is from 1 to 6 on one or both of the 5' ends of the duplexed strands. In another embodiment, the number of overhanging nucleotides is zero. In one embodiment, each of the strands is 19 nucleotides in length, fully hybridizable with the complementary strand, and includes no overhangs. In other embodiments, each of the strands is 21 nucleotides in length, and 19 nucleotides are fully hybridizable with the complementary strand and each strand has a 2-nucleotide overhang at the 3' end.

Generally, each strand of the NRG-1 siRNA duplex is from about 12 to about 35 nucleotides. In some embodiments, each strand of the NRG-1 siRNA duplex is about 17 to about 25 nucleotides. In some embodiments, each strand of the NRG-1 siRNA duplex is about 19 to about 21 nucleotides in length. The central complementary portion may be from about NRG-1 12 to about 35 nucleotides in length. In one embodiment, the central complimentary portion is about 17 to about 25 nucleotides in length, or about 19 to about 21 nucleotides in length. It is understood that each strand of the NRG-1 siRNA duplex and the central complementary portion may be about 12, 13, 14, 15, 16, 17, 18, 19, 20, 21, 22, 23, 24, 25, 26, 27, 28, 29, 30, 31, 32, 33, 34, or 35 nucleotides in length. In particular embodiments, the siRNAs can have about 12, 13, 14, 15, 16, 17, 18, 19, 20, 21, 22, 23, 24, 25, 26, 27, 28, 29, 30, 31, 32, 33, 34, or 35 contiguous nucleotides of the nucleic acid sequence set forth by SEQ ID NO: 8 as well as the complement or reverse complement of such sequence. For example, the siRNAs can have about 12, 13, 14, 15, 16, 17, 18, 19, 20, 21, 22, 23, 24, 25, 26, 27, 28, 29, 30, 31, 32, 33, 34, or contiguous nucleotides of the nucleic acid sequence which encodes the EGF domain of NRG-1 (e.g., nucleic acids 1085 to 1180 of SEQ ID NO: 8) as well as the complement or reverse complement of such sequence. The terminal portions of siRNAs can be from 1 to 6 nucleotides. It is understood that the terminal portions can be about 1, 2, 3, 4, 5, or 6 nucleotides in length. The NRG-1 siRNAs may also have no terminal portions. The two strands of a NRG-1 siRNA can be linked internally leaving free 3' or 5' termini, or can be linked to form a continuous hairpin structure or loop. The hairpin structure may contain an overhang on either the 5' or 3' terminus producing an extension of single-stranded character.

Each of the above-described antisense compounds provides sequence-specific target gene regulation. This sequence-specificity makes antisense compounds effective tools for the selective modulation of a target nucleic acid of interest, such NRG-1.

In some examples, the antisense compounds described herein contain one or more modifications to enhance nuclease resistance and/or increase activity of the compound. Modified antisense compounds include those comprising modified backbones or non-natural internucleoside linkages. As defined herein, antisense compounds having modified backbones include those that retain a phosphorus atom in the backbone and those that do not have a phosphorus atom in the backbone. Examples of modified oligonucleotide backbones include, but are not limited to, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, and boranophosphates having normal 3'-5' linkages, 2'-5' linked analogs of these, and those having inverted polarity wherein the adjacent pairs of the nucleoside units are linked 3'-5' to 5'-3' or 2'-5' to 5'-2'. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Examples of modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In some embodiments, both the sugar and the internucleoside linkage of the nucleotide units of the antisense compound are replaced with novel groups. One such modified compound is an oligonucleotide mimetic referred to as a peptide nucleic acid (PNA). In PNA compounds, the sugar-backbone of an oligonucleotide is replaced with an amide containing backbone, in particular an aminoethylglycine backbone. The bases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262. Further teaching of PNA compounds can be found in Nielsen et al. (*Science* 254, 1497-1500, 1991).

Modified antisense compound can also contain one or more substituted sugar moieties. In some examples, the antisense compounds can comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In other embodiments, the antisense compounds comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one example, the modification includes 2'-methoxyethoxy (also known as 2'-O-(2-methoxyethyl) or 2'-MOE) (Martin et al., *Helv. Chim. Acta.*, 78, 486-504, 1995). In other examples, the modification includes 2'-dimethylaminooxyethoxy (also known as 2'-DMAOE) or 2'-dimethylaminoethoxyethoxy (also known in the art as 2'-β-dimethylaminoethoxyethyl or 2'-DMAEOE).

Similar modifications can also be made at other positions of the compound. Antisense compounds can also have sugar mimetics such as cyclobutyl moieties in place of the pentofuranosyl sugar. Representative United States patents that teach the preparation of modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Antisense compounds can also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further modified bases have been described (see, for example, U.S. Pat. No. 3,687,808; and Sanghvi, Y. S., Chapter 15, Antisense Research and Applications, pages 289-302, Crooke, S. T. and Lebleu, B., ed., CRC Press, 1993). Certain of these modified bases are useful for increasing the binding affinity of antisense compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. Representative U.S. patents that teach the preparation of modified bases include, but are not limited to, U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,750,692.

IV. Pharmaceutical Compositions

The NRG-1 agonists or inhibitors/antagonists disclosed herein may be included in pharmaceutical compositions (including therapeutic and prophylactic formulation), typically combined together with one or more pharmaceutically acceptable vehicles or carriers, and optionally, other therapeutic ingredients. Typically, the composition includes a pharmaceutically acceptable carrier when the composition is used as described below in "Methods of Use." The NRG-1 agonists or inhibitors/antagonists disclosed herein may be combined and/or used in combination with other therapeutic agents, different from the subject NRG-1 agonists or inhibitors/antagonists depending on the specific condition or disease being treated.

Pharmaceutical compositions including a disclosed NRG-1 agonist or inhibitor/antagonist can be administered to subjects by a variety of modes, including topical administration, parental administration (for instance intramuscular, intraperitoneal, or intravenous), oral, transdermal, nasal, or aerosol. The formulations may be conveniently presented in unit dosage form and may be prepared by methods well known in the art of pharmacy. Methods of preparing a pharmaceutical composition include associating the active compound (e.g., a disclosed NRG-1 peptide, antibody, or RNAi) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

The compositions can be administered as needed, such as at least once per day. The amount of active ingredient that may be combined with the carrier materials to produce a single dosage form will vary depending upon the subject treated and the particular mode of administration. A typical preparation can contain from about 5% to about 95% active compound (w/w). In one example, such preparations contain from about 20% to about 80% active compound. The amount of active compound in such therapeutically useful compositions is such that the dosage level will be effective to prevent or suppress the condition the subject has or is at risk for. Such conditions are described herein.

Formulations suitable for topical administration can include dusting powders, ointments, cremes, gels or sprays for the administration of the active compound to cells, such as skin cells. Such formulations may optionally include an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, free radical scavenger, ultraviolet light blocker, sunscreen agents, preservative, fragrance, thickener, or combinations thereof.

As one example, the active compounds of the present disclosure can be used in cosmetic formulations (e.g., skincare cream, sunscreen, decorative make-up products, and other dermatological compositions) in various pharmaceutical dosage forms, and especially in the form of oil-in-water or water-in-oil emulsions, solutions, gels, or vesicular dispersions. The cosmetic formulations may take the form of a cream which can be applied either to the face or to the scalp and hair, as well as to the human body, in particular those portions of the body that are chronically exposed to sun. They can also serve as a base for a lipstick.

In some cosmetic formulations, additives can be included such as, for example, preservatives, bactericides, perfumes, antifoams, dyes, pigments which have a coloring action, surfactants, thickeners, suspending agents, fillers, moisturizers, humectants, fats, oils, waxes or other customary constituents of a cosmetic formulation, such as alcohols, polyols, polymers, foam stabilizers, electrolytes, organic solvents, or silicone derivatives.

Cosmetic formulations typically include a lipid phase and often an aqueous phase. The lipid phase can be chosen from the following group of substances: mineral oils, mineral waxes, such as triglycerides of capric or of caprylic acid, castor oil; fats, waxes and other natural and synthetic fatty substances, esters of fatty acids with alcohols of low C number, for example with isopropanol, propylene glycol or glycerol, or esters of fatty alcohols with alkanoic acids of low C number or with fatty acids; alkyl benzoates; silicone oils, such as dimethylpolysiloxanes, diethylpolysiloxanes, diphenylpolysiloxanes and mixed forms thereof.

If appropriate, the aqueous phase of the formulations according to the present disclosure include alcohols, diols or polyols of low C number and ethers thereof, such as ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, such as silicon dioxide, aluminium silicates, polysaccharides and derivatives thereof, for example hyaluronic acid, xanthan gum and hydroxypropyl-methylcellulose, or poly-acrylates.

An exemplary cosmetic formulation is a sunscreen composition. A sunscreen can additionally include at least one further UVA filter and/or at least one further UVB filter and/or at least one inorganic pigment, such as an inorganic micropigment. The UVB filters can be oil-soluble or water-soluble. Oil-soluble UVB filter substances can include, for example: 3-benzylidenecamphor derivatives, such as 3-(4-methylbenzylidene)camphor and 3-benzylidenecamphor; 4-aminobenzoic acid derivatives, such as 2-ethylhexyl 4-(dimethylamino)benzoate and amyl 4-(dimethylamino)benzoate; esters of cinnamic acid, such as 2-ethylhexyl 4-methoxycinnamate and isopentyl 4-methoxycinnamate; derivatives of benzophenone, such as 2-hydroxy-4-methoxybenzophenone, 2-hydroxy-4-methoxy-4'-methylbenzophenone and 2,2'-dihydroxy-4-methoxybenzophenone; esters of benzalmalonic acid, such as di(2-ethylhexyl)-4-methoxybenzalmalonate. Water-soluble UVB filter substances can include the following: salts of 2-phenylbenzimidazole-5-sulphonic acid, such as its sodium, potassium or its triethanolammonium salt, and the sulphonic acid itself; sulphonic acid derivatives of benzophenones, such as 2-hydroxy-4-methoxybenzophenone-5-sulphonic acid and salts thereof; sulphonic acid derivatives of 3-benzylidenecamphor, such as, for example, 4-(2-oxo-3-bornylidenemethyl)benzenesulphonic acid, 2-methyl-5-(2-oxo-3-bornylidenemethyl)benzenesulphonic acid and salts thereof. The list of further UVB filters mentioned which can be used in combination with the active agent(s) according to the disclosure is not intended to be limiting.

An additional exemplary cosmetic formulation is a composition for darkening skin color, such as a self-tanning lotion, and thus includes one or more NRG-1 agonists.

Formulations for parenteral administration include a sterile aqueous preparation of the composition, or dispersions of sterile powders that include the composition, which in an example are isotonic with the blood of the recipient. Isotonic agents that can be included in the liquid preparation include sugars, buffers, and sodium chloride. Solutions of the composition can be prepared in water, and optionally mixed with a nontoxic surfactant. Dispersions of the composition can be prepared in water, ethanol, a polyol (such as glycerol, propylene glycol, liquid polyethylene glycols, and the like), vegetable oils, glycerol esters, and mixtures thereof. The final dosage form can be sterile, fluid and stable under the conditions of manufacture and storage. The desired fluidity can be achieved, for example, by using liposomes, by employing the appropriate particle size in the case of dispersions, or by using surfactants. Sterilization of a liquid preparation can be achieved by any convenient method that preserves the bioactivity of the composition, such as by filter sterilization. Methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the composition by the animal over a prolonged period can be achieved by including agents for delaying, for example, aluminum monostearate and gelatin.

Formulations of the present disclosure suitable for oral administration may be presented as discrete units such as tablets, troches, capsules, lozenges, wafers, or cachets, each containing a predetermined amount of the active compound as a powder or granules, as liposomes containing the active compound, or as a solution or suspension in an aqueous liquor or non-aqueous liquid such as a syrup, an elixir, an emulsion or a draught.

The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, fructose, lactose or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active compound can be incorporated into sustained-release preparations and devices.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the NRG-1 agonist or antagonist/inhibitor and methods of the present disclosure include humans, as well as non-human primates and other animals. To identify subjects for prophylaxis or treatment according to the methods of the disclosure, accepted screening methods are employed to determine risk factors associated with a targeted or suspected disease of condition (for example, skin cancer) or to determine the status of an existing disease or condition in a subject. These screening methods include, for example, diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure.

The administration of a NRG-1 agonist or antagonist/inhibitor of the disclosure can be for prophylactic, therapeutic and/or cosmetic purposes. When provided prophylactically, the NRG-1 peptide is provided in advance of any symptom. The prophylactic administration of the compound serves to prevent or ameliorate any subsequent disease process. When provided therapeutically, the compound is provided at (or shortly after) the onset of a symptom of disease or infection. When provided cosmetically, the NRG-1 peptide is provided as desired by the user (such as to lighten skin color, darken skin or other cosmetic purposes).

For prophylactic, therapeutic and cosmetic purposes, the NRG-1 agonist or antagonist/inhibitor can be administered to the subject such as by topical delivery over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies or human model studies accepted by those of ordinary skill in the art to be representative of in vivo studies followed up by human clinical trials and is guided by administration protocols that significantly reduce the occurrence or severity of targeted disease symptoms or conditions in the subject. Suitable models in this regard include, for example, murine (such as a nude mouse model with a human skin graft), rat, porcine, guinea pig, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of a NRG-1 agonist or antagonist (for example, amounts that are effective to alleviate one or more symptoms of a targeted disease or condition or to prevent UV skin damage). In alternative embodiments, an effective amount or effective dose of a NRG-1 peptide may simply inhibit or enhance one or more selected biological activities correlated with a disease or condition.

The actual dosage of a NRG-1 agonist or antagonist/inhibitor will vary according to factors such as the disease indication and particular status of the subject (for example, the subject's age, size, fitness, extent of symptoms, susceptibility factors, and the like), time and route of administration, other drugs or treatments being administered concurrently. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. Dosages of the pharmaceutical compositions of the presented disclosure are typically from about 0.01 mg/kg up to about 0.10 mg/kg. Generally a suitable dose is about 1 milligram per kilogram (mg/kg) to about 50 mg/kg, such as a dose of about 1 mg/kg, about 2 mg/kg, about 5 mg/kg, or about 20 mg/kg administered parenterally. For example, a suitable dose is about 1 mg/kg to about 100 mg/kg, such as a dose of about 1 mg/kg, about 10 mg/kg, about 20 mg/kg, about 50 mg/kg, or about 100 mg/kg administered orally. Unit dosage forms are also possible, for example 50 mg, 100 mg, 150 mg or 200 mg, or up to 400 mg per dose. However, other higher or lower dosages also could be used, such as from about 0.001 mg/kg to about 1 g/kg, such as about 0.1 to about 500 mg/kg, including about 0.5 mg/kg to about 200 mg/kg. In particular examples, a therapeutically effective dose of an agent including a disclosed NRG-1 agonist or antagonist is at least 1 µg daily (such as 1-100 µg or 5-50 µg) if administered via injection, or at least 1 mg daily if administered topically (such as 1-100 mg or 5-50 mg). In one example, a therapeutically effective dose is between 1 ng/ml to 500 ng/ml, such as between 20 ng/ml to 100 ng/ml, including about 10 ng/ml, about 20 ng/ml, about 30 ng/ml, about 40 ng/ml, about 50 ng/ml, about 60 ng/ml, about 70 ng/ml, about 80 ng/ml, about 90 ng/ml or about 100 ng/ml administered topically. In particular examples, such daily dosages are administered in one or more divided doses (such as 2, 3, or 4 doses) or in a single formulation. The disclosed agents can be administered alone, in the presence of a pharmaceutically acceptable carrier, in the presence of other therapeutic agents (such as other antineoplastic agents), or both.

Dosage can be varied by the attending clinician to maintain a desired concentration at a target site. Higher or lower concentrations can be selected based on the mode of delivery, for example, topical, trans-epidermal, rectal, oral, pulmonary, intranasal delivery, intravenous or subcutaneous delivery. Dosage can also be adjusted based on the release rate of the administered formulation, for example, sustained release oral versus injected particulate or transdermal delivery formulations, and so forth. To achieve the same serum concentration level, for example, slow-release particles with a release rate of 5 nM (under standard conditions) would be administered at about twice the dosage of particles with a release rate of 10 nM.

V. Methods of Use

It is shown herein that melanogenic factors secreted from fibroblasts regulate constitutive skin color and possibly its dysfunction in pigmentary skin diseases. For example, NRG-1 was identified as a melanogenic factor regulating the constitutive pigmentation of darker human skin. Based on this observation, methods of modulating pigmentation and proliferation of a melanocyte by modulating NRG-1 activity, such as to prevent or treat skin disorders, including skin cancer, or to alter skin color, such as for cosmetic purposes, are disclosed. In one example, a method of modulating pigmentation of a melanocyte includes contacting the melanocyte (e.g., a melanocyte present in a mammal, such as a human melanocyte) with a composition including one or more disclosed agents that modulates NRG-1 activity (such as a therapeutically effective concentration of one or more compositions including any one of the disclosed NRG-1 peptides, antisense compounds or antibodies), thereby modulating pigmentation of the melanocyte.

Modulation of NRG-1 activity includes increasing or decreasing NRG-1 nucleic acid expression, NRG-1 protein expression, NRG-1 protein biological activity or a combination thereof. In one example, modulating activity of NRG-1 includes increasing nucleic acid expression, protein expression, protein biological activity or combination thereof as compared to NRG-1 nucleic acid expression, protein expression, protein biological activity or combination thereof in an untreated cell. In other examples, modulating activity of NRG-1 includes reducing and or inhibiting nucleic acid expression, protein expression, protein biological activity or combination thereof as compared to NRG-1 nucleic acid expression, protein expression, protein biological activity or combination thereof in an untreated cell. In an example, contacting the cell with one or more agents comprises administering the one or more agents to the mammal, such as a human.

In particular examples, an agent that modulates NRG-1 activity is an agent that increases NRG-1 activity, such as an NRG-1 antibody, an NRG-1 coding sequence or a functional fragment thereof, or a NRG-1 protein or functional fragment thereof. In one example, the method of increasing melanocyte pigmentation or proliferation is used to reduce UV skin damage and skin cancer (such as by increasing normal melanocyte proliferation and or pigmentation, thus decreasing a subject's risk to develop skin cancer). In some examples, the method of increasing melanocyte pigmentation or proliferation is used darken skin color, such as desired for aesthetic purposes. Thus, in some examples a human subject with UV skin damage or who has an increased risk for UV skin damage is selected for treatment with an NRG-1 agonist.

In other examples, an agent that modulates NRG-1 activity is an agent that decreases NRG-1 activity, such as an NRG-1 inhibitory RNA molecule or NRG-1 inhibitory antibody. For example, the method includes decreasing melanocyte pigmentation via inhibition of NRG-1 activity to treat a skin pigmentation disorder associated with undesired increased skin pigmentation. In other examples, the method includes decreasing melanocyte pigmentation via inhibition of NRG-1 activity for cosmetic purposes, such as to lighten a subject's skin color.

Also disclosed are methods of treating a melanoma. In one example, methods of treating a melanoma include administering to a subject a therapeutically effective amount of an agent that decreases NRG-1 activity (such as an NRG-1 inhibitory RNA molecule or NRG-1 inhibitory antibody) in a melanoma cell as compared to NRG-1 activity in such cell in the absence of the agent, thereby treating one or more signs or symptoms associated with the melanoma.

In a particular example, the compound or a pharmaceutical composition comprising the compound readily penetrates the skin when topically administered. Compounds of this disclosure which cannot penetrate the skin can be effectively administered by alternative routes including injection. In a further example, the pharmaceutical composition includes a compound of the disclosure and a pharmaceutically acceptable carrier that allows it to penetrate the skin, such as a liposome.

In some examples, the methods of use can include selecting a subject in need of treatment. For example, studies can be performed to identify a subject as being afflicted with a skin disorder, including, but not limited to, any of the skin disorders described herein. In one example, the skin disorder is UV skin damage. In other examples, the skin disorder is one associated with undesirable dark pigmentation spots. In further examples, the skin disorder is skin cancer such as melanoma. Methods of detecting a skin disorder including those described herein are known to those of skill in the art and can include methods of measuring cell proliferation and or pigmentation as described herein.

Therapeutically Effective Concentration

In the methods disclosed herein, a therapeutically effective amount of an agent capable of modulating NRG-1 activity is administered to a subject with a skin disorder, such as skin cancer (e.g., melanoma), UV damage, or having undesired hyper or hypo skin pigmentation. Assays to determine a therapeutically effective amount of an agent for inhibiting or reducing one or more signs or symptoms associated with a skin disorder are well known in the art.

In some examples, a therapeutic effective amount of an agent is one in which one or more signs or symptoms associated with a skin disorder, such as UV skin damage or undesired dark skin pigmentation, is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the agent.

For example, a therapeutic effective amount of an agent is one in which cell proliferation is modulated, such as increased or decreased (depending upon the condition), such as an increase or decrease by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, than proliferation in the absence of the agent. In some examples, the increase or decrease is an increase or decrease by at least 2-fold, at least 3-fold, at least 5-fold, at least 10-fold, including about a 2-fold, 3-fold, 4-fold, 5-fold, 6-fold, 8-fold, 10-fold, 20-fold, 50-fold increase or decrease, than proliferation in the absence of the agent. Methods of assessing cell proliferation are known to one skilled in the art, including those described herein as well as commercially available cell proliferation assay kits (such as from Invitrogen, Carlsbad, Calif.).

In other examples, a therapeutic effective amount of an agent is one in which cell pigmentation is modulated (increased or reduced depending upon the condition), such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, difference than cell pigmentation in the absence of the agent. In some examples, the increase or decrease is an increase or decrease by at least 2-fold, at least 3-fold, at least 5-fold, at least 10-fold, including about a 2-fold, 3-fold, 4-fold, 5-fold, 6-fold, 8-fold, 10-fold, 20-fold, 50-fold increase or decrease, than cell pigmentation in the absence of the agent. Methods of assessing cell pigmentation are known to one skilled in the art, including those described herein as well as those that use commercially available synthetic melanin (such as from Sigma Aldrich, St. Louis, Mo.) which is used to construct a standard curve for the melanin assay.

In some examples, a therapeutic effective amount of a disclosed pharmaceutical composition is one in which NRG-1 expression or activity is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the composition. In some examples, NRG-1 expression or activity is reduced or inhibited by at least 2-fold, at least 3-fold, at least 5-fold, at least 10-fold, including about a 2-fold, 3-fold, 4-fold, 5-fold, 6-fold, 8-fold, 10-fold, 20-fold, 50-fold decrease, than NRG-1 expression or activity in the absence of the agent. Methods of assessing NRG-1 expression are known to one skilled in the art, including those described in the Examples below (e.g., Western blot assay with commercially available antibodies).

In some examples, a therapeutic effective amount of a disclosed pharmaceutical composition is one in which NRG-1 expression or activity is increased, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, more than expression or activity in the absence of the composition. In some examples, NRG-1 expression or activity is reduced or inhibited by at least 2-fold, at least 3-fold, at least 5-fold, at least 10-fold, including about a 2-fold, 3-fold, 4-fold, 5-fold, 6-fold, 8-fold, 10-fold, 20-fold, 50-fold increase, than NRG-1 expression or activity in the absence of the agent.

In further examples, a therapeutic effective amount of a disclosed pharmaceutical composition is one in which ERBB activity or expression, such as ERBB2, ERBB3, ERBB4 or a combination thereof activity or expression is altered, such as increased or decreased, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, as compared to activity or expression in the absence of the composition. Methods of assessing ERBB2, ERBB3, and/or ERBB4 expression and activity are known to one skilled in the art, including those described in the Examples below (e.g., Western blot assay with commercially available antibodies).

Dosages, routes of administration of the disclosed pharmaceutical compositions for the methods of treatment are known to those of skill in the art and include, but are not limited to those described herein, including Section IV and the Examples.

Exemplary Skin Disorders

Exemplary skin disorders, include, but are not limited to, skin cancer (such as melanoma and metastasis melanoma), undesired dark skin pigmentation (such as age spots and post-inflammatory hyperpigmentation), or a combination thereof. In one particular example, the skin disorder is melanoma. In another example, the skin disorder is undesired dark skin pigmentation. The disclosed compositions and methods can be used to treat additional skin disorders including those disclosed in Hearing and Leong (From Melanocyte to Melanoma: The Progression to Malignancy, N.Y.: Humana Press, 2005), Nordlund et al., (The Pigmentary System: Physiology and Pathophysiology, Edinburgh: Blackwell Science, 2006), and Levine (Pigmentation and Pigmentary Disorders, Boca Raton: CRC Press, 1993) each of which is incorporated by reference in its entirety.

VI. Kits

Provided by this disclosure are kits that can be used to treat a skin disorder. For example, a kit is disclosed herein for preventing or inhibiting a skin disorder, such as skin cancer, by reducing or inhibiting one or more symptoms associated with a skin disorder in which the kit includes at least one of the disclosed pharmaceutical compositions. The disclosed kits can include instructional materials disclosing means of use of the compositions in the kit. The instructional materials can be written, in an electronic form (such as a computer diskette or compact disk) or can be visual (such as video files). One skilled in the art will appreciate that the kits can include other agents to facilitate the particular application for which the kit is designed. The disclosed kits can include an applicator for applying the composition to the desired surface, such as skin.

In some examples, the kit also includes additional sunscreen agents. In some examples, the kit is a kit for self-tanning.

In one example, a kit is provided for treating a skin disorder, such as melanoma or undesired increased pigmentation. For example, such kits can include one or more of the disclosed pharmaceutical compositions including one or more of the disclosed NRG-1 peptide fragments.

The present disclosure is illustrated by the following non-limiting Examples.

EXAMPLES

Example 1

Materials and Methods

This example describes the materials and methods used for the studies disclosed herein.

Human Fibroblast and Melanocyte Cultures.

Adult human fibroblasts derived from the dermis of 4 mm punch biopsies taken from the lower backs of 15 healthy subjects of 3 different phototypes (types I, III and VI). Subjects with type I skin were #4, 12, 15, 19 and 26; subjects with type III skin were #6, 9, 13, 14 and 23, and subjects with type VI skin were #7, 8, 16, 17 and 18. The fibroblasts were cultured from the biopsies and were grown in monolayer culture in high glucose Dulbecco's modified Eagle medium (DMEM) supplemented with 10% fetal bovine serum (FBS) and 1% L-glutamine plus 1% penicillin and streptomycin at 37° C. in a humidified 5% $CO_2$ atmosphere. Fibroblasts were subcultured using routine methods and were used at passages 3 to 6.

Human neonatal epidermal melanocytes, lightly and darkly pigmented (HEM-LP and HEM-DP, respectively) were obtained from Cascade Biologics (Portland, Oreg.) and were cultured in melanocyte growth medium (MGM) consisting of Medium 254 and human melanocyte growth supplement (both from Cascade Biologics) at 37° C. under 5% $CO_2$. Melanocytes from the third to ninth passage were used in these studies.

Microarray Procedures.

Oligo-cDNA microarray hybridization was performed according to the National Cancer Institute in-house protocol, as detailed previously (Yamaguchi et al., 2008). Briefly, total RNAs were prepared from cultured fibroblasts using an RNeasy mini kit (Qiagen, Valencia, Calif.). The quality (purity and integrity) and quantity of each total RNA preparation was measured using a Nanodrop ND-1000 spectrophotometer (Thermo Scientific, Wilmington, Del.). A universal human reference RNA (Stratagene, La Jolla, Calif.) was used as a control. cDNA samples generated from RNA samples and purified before the coupling reaction were labeled with Cy3 (for fibroblast samples) or Cy5 (for reference RNA) monoreactive dyes (GE Healthcare, Piscataway, N.J.), and were hybridized simultaneously on an oligo-DNA chip (Hs-OperonV3.0-v1p24, p27, p31) overnight at 42° C. Two fluorescent intensities of the oligo-DNA chip were scanned using a microarray scanner (GenePix 6100A; Axon Instruments Inc., Molecular Devices Corp., Sunnyvale, Calif.). Differential gene expression was profiled using Genepix Pro 5.0 software and was analyzed by Miltenyi Biotec (Bergisch Gladbach, Germany). The full microarray database is available at GEO (GSE22022).

shRNA Transduction.

Control shRNA lentiviral particles (sc-108080) and NRG-1 shRNA (sc-37210-V) were purchased from Santa Cruz Biotechnology (Santa Cruz, Calif.), and were transduced to fibroblasts derived from type VI skin (#8, 17 and 28) according to the manufacturer's instructions. Briefly, cells were plated at 50,000 cells/well in 6 well plates 24 hrs prior to viral infection. The next day, cells were transduced with lentiviral particles (MOI=4) in the presence of 2 µg/ml polybrene (Santa Cruz). Selection with puromycin (2 µg/ml) was performed for 10 days in normal fibroblast growth medium; normal fibroblasts without shRNA transduction did not survive under this selection condition. Stably transduced puromycin-resistant cells were subcultured and expanded for the confirmation of NRG-1 knock-down and also for further studies.

3-Dimensional Skin Reconstructs.

Light (from Caucasian skin), Medium (from Asian skin), and Dark (from African-American skin) human epidermal equivalents (MelanoDerm®) were purchased from MatTek Corp. (Ashland, Mass.). MelanoDerms were grown at the air/liquid interface of the maintenance medium MEL-LLMM (MatTek Corp.), and the culture medium was renewed every 2 days. Where noted, MelanoDerms were treated for 9 days with 50 ng/ml NRG-1 (rhNRG-1-β1, R&D Systems, Minneapolis, Minn.) prepared in phosphate-buffered saline (PBS) with 0.1% bovine serum albumin (BSA) and MelanoDerm maintenance medium. The same concentrations of PBS and BSA were used for mock-treated controls.

For the studies where the MelanoDerms were co-cultured with shRNA transduced fibroblasts, NRG-1 shRNA transduced fibroblasts or control shRNA transduced fibroblasts from type VI skin were grown in normal fibroblast growth medium, and the Dark MelanoDerms were placed on top of the confluent monolayer culture in the MelanoDerm maintenance medium. Every 2 days, MelanoDerms were transferred to a freshly prepared confluent fibroblast culture in the fresh MelanoDerm maintenance medium, and MelanoDerms were harvested after 9 days of treatment.

For the studies where the MelanoDerms were treated with NRG-1 and/or various pan-ERBB inhibitors, Dark MelanoDerms were first incubated with a pan-ERBB inhibitor (0.5 µM Compound 39, EMD Chemicals, Gibbistown, N.J. or 2 µM CI-1033, Selleck Chemicals LLC, US) for 30 minutes or with vehicle (DMSO) only before treatment with 50 ng/ml NRG-1; identical amounts of DMSO (0.02%) were added to all samples. Treatment was renewed every 2 days in fresh medium and was continued for 9 days.

Western Blotting Analysis.

Fibroblast cultures in 100-mm dishes were solubilized in appropriate volumes of M-PER mammalian protein extraction reagent (Pierce Biotechnology, Rockford, Ill.) containing a Protease Inhibitor mixture (Roche, Mannheim, Germany) and phosphatase inhibitors. The protein concentration of each extract was measured using a BCA protein assay kit (Pierce, Rockford, Ill.). Cell extracts (20 µg) were separated on 8-16% gradient SDS polyacrylamide gels (Invitrogen, Carlsbad, Calif.), after which proteins were transferred to PVDF membranes (Invitrogen, Carlsbad, Calif.). Membranes were blocked for 1 hour in PBS or Tris buffered saline (TBS) containing 0.1% Tween 20 and 5% (w/v) nonfat dry milk powder and were incubated overnight at 4° C. with the primary antibody in PBS containing 0.1% Tween 20 and 2.5% (w/v) nonfat dry milk powder or in 0.1% Tween-TBS with 5% BSA, depending on the antibody. The following primary antibodies were used: anti-human DKK-1 (0.2 µg/ml), anti-human DKK-3 (0.1 µg/ml), anti-human bFGF (0.1 µg/ml), anti-human SCF (0.1 µg/ml), anti-human mouse monoclonal ERBB3 (1 µg/ml) and anti-human mouse monoclonal ERBB4 (2 µg/ml) antibodies from R&D Systems, neuregulin-1α/β1/2 (C-20) (1:500) and GAPDH (FL-335) (1:10,000)

antibodies from Santa Cruz Biotechnology, ERBB2 rabbit monoclonal (1:1000) and phospho-Akt (Ser473) (1:1000) antibodies from Cell Signaling Technology. Membranes were then incubated with an HRP-linked anti-rabbit antibody (GE Healthcare) at 1:10,000 dilution or with an anti-goat antibody (DAKO) at 1:2,000 dilution at room temperature for 1 hour. Antigen-antibody complexes were detected using an ECL-plus Western blotting detection system (GE Healthcare). Each study was performed at least in triplicate.

Immunohistochemical Staining.

Fibroblasts were cultured in two-well Lab-Tek chamber slides (Nalge Nunc International Corp., Naperville, Ill.) and were processed for indirect fluorescence to detect the expression of proteins using two different primary antibodies to NRG-1 (rabbit polyclonal, 20 µg/ml, Abcam; neuregulin-1α/β1/2 (C-20), 2 µg/ml, Santa Cruz). Bound antibodies were visualized with Alexa Fluor 594 goat anti-rabbit IgG (H+L) (Molecular Probes, Eugene, Oreg.), at 25° C. for 1 hour at a 1:400 dilution with 5% goat serum. Nuclei were counter-stained with DAPI (Vector Laboratories). The red fluorescence produced by Alexa 594 and blue fluorescence by DAPI were observed and captured using a Leica DMR B/D MLD fluorescence microscope (Leica, Wetzlar, Germany) and a Dage-MTI 3CCD 3-chip color video camera (Dage-MTI, Michigan City, Ind.).

Immunohistochemistry and Melanin Staining.

The expression of NRG-1 in frozen sections of skin specimens from the same volunteers from whom the fibroblasts were derived was detected by indirect immunofluorescence with the primary antibody to NRG-1 (rabbit polyclonal, 20 µg/ml, Abcam). Bound antibodies were visualized with Alexa Fluor 594 goat anti-rabbit IgG (H+L) at 25° C. for 1 hour at a 1:400 dilution with 5% normal goat serum. Fluorescence was observed and analyzed with a fluorescence microscope as detailed above. Paraffin-embedded tissues were also processed for the Fontana-Masson silver stain to observe the melanin distribution in skin specimens.

Melanin Content Assay.

Melanin contents were determined by dissolving cell pellets overnight at room temperature in 200 µl 1 N NaOH, and melanin concentrations were quantitated by absorbance at 405 nm in a SpectraMax 250 ELISA reader (Molecular Devices) using a standard curve generated from synthetic melanin (Sigma-Aldrich, St. Louis, Mo.). Melanin content is expressed as µg melanin per µg protein. Each study was repeated at least three times.

RT-PCR.

Total RNAs were isolated from cells using an RNeasy mini kit (Qiagen, Valencia, Calif.), and 500 ng RNA of each sample was used for reverse transcription. The following primers were used for PCR: human ERBB2 sense primer 5'-acagtggcatctgtgagctg-3' (SEQ ID NO: 1); ERBB2 antisense primer 5'-agcagaggtgggtgttatgg-3' (SEQ ID NO: 2); NRG-1 sense primer 5'-ctgtgtgaatggaggggagt-3' (SEQ ID NO: 3); NRG-1 antisense primer 5'-gcttttccgctgtttcttg-3' (SEQ ID NO: 4); glyceraldehyde-3-phosphate dehydrogenase (GAPDH) sense primer 5'-accacagtccatgccatcac-3' (SEQ ID NO: 5); GAPDH antisense primer 5'-tccaccaccctgt-tgctgta-3' (SEQ ID NO: 6). After denaturation at 94° C. for 3 min, PCR was performed for 32 cycles for ERBB2, 29 cycles for NRG-1, and 28 cycles for GAPDH (30 sec at 94° C., 30 sec at 60° C., and 45 sec at 68° C.). Control reactions were performed in the absence of reverse transcriptase and were negative. Each study was repeated in duplicate independently.

Statistical Analysis.

The LIMMA package in R BioConductor was used for microarray analysis. Each array was subjected to two types of normalization, a nonlinear locally weighted scatterplot smoothing (LOWESS) normalization, which corrects intensity-dependent variation in dye bias, and a quantile normalization to ensure all reference channels having the same empirical distribution across arrays, leaving the M-values (log-ratios) un-changed. Differential expression between groups was assessed using linear models and empirical Bayes methods provided by LIMMA. Spots with absolute logarithm based 2 of fold change ratio >1.5 and a t-statistics-based p-value of <0.05 were retained for further exploration.

Example 2

Microarray Analysis of Expression Patterns of Fibroblasts from Different Skin Types This example illustrates gene expression patterns of fibroblasts were not found to significantly vary amongst skin type.

Gene expression patterns of 15 different primary fibroblast cell lines derived from skin biopsies from the lower back skin of individuals of 3 different skin types (5 each from skin phototypes I, III and VI) were analyzed using the Operon V3.0 human whole genome spotted microarray platform. Eleven thousand seven hundred and seventy one out of 36,288 spots were filtered with at least half of the corresponding intensity measures (CIMs) less than the mean of the background signal of the array plus three times the standard deviation of the background for further analysis. Clustering analysis did not yield strong evidence of distinct gene expression profiles among the three skin types.

Example 3

Expression Patterns of Known Fibroblast-Derived Melanogenic Paracrine Factors

This example illustrates the expression of known fibroblast-derived melanogenic paracrine factors depend upon skin phototype.

Fibroblast-derived melanogenic paracrine factors that were identified in earlier studies were measured to see if any of them were regulated differently depending on the skin phototypes from which the fibroblasts had been derived (FIG. 1). Stem cell factor (SCF) and basic fibroblast growth factor (bFGF) are known melanogenic paracrine factors especially with respect to responses to UV exposure. Neither of these factors showed different expression patterns in the various skin types. Dickkopf-1 (DKK1) is a paracrine factor responsible for topographical differences of skin color in palm versus trunk skin, but although there was quite a variation in expression patterns of DKK1 and the related dickkopf-3 (DKK3), neither of those showed expression patterns that consistently correlated with skin phototype.

Example 4

Enrichment of Secreted Genes in Differential Expression Analysis Between Type I or III and Type VI Skins This example demonstrates that certain secreted genes are differentially expressed amongst type I or III and type VI skin.

Fibroblasts regulate the distinctive pigmented and thick morphology of skin on the palms and soles compared to the remainder of the body via a factor they secrete termed DKK1. In a study, fibroblasts derived from type I or type III skin were found to significantly inhibit the pigmentation of Melano-Derm skin while fibroblasts derived from type VI skin have lesser effects (summarized in Table 1A below).

TABLE 1A

Effects of fibroblast on pigmentation of MelanoDerm Skin Model. Fibroblasts from 3 different subjects for each skin type (I, III or VI) were used (n = 3). Lipoic acid represents treatment with 30 μM lipoic acid used as a positive control. Control represents treatment with no fibroblasts as a negative control. Viability was measured using the MTT assay and melanogenesis was evaluated using the L-[$_{14}$C]tyrosine assay; Results are shown as means ± SEM.

| Control | Viability 100% | Melanogenesis 100% |
|---|---|---|
| Skin type I | 107 ± 11% | 65 ± 18% |
| Skin type III | 103 ± 4% | 66 ± 20% |
| Skin type VI | 91 ± 19% | 93 ± 22% |
| Lipoic acid | 88 ± 14% | 2 ± 2% |

The role that fibroblasts play in regulating the constitutive skin color of different phenotypes via their secreted factors was investigated. Among the 24,517 genes used for analysis, there were 1,178 genes that are secreted based on UniProtKB keywords. Among the total of 50 genes having differential expression between type I or III skin and type VI skin based on the following criteria: i) p-value <0.05, and ii) absolute logarithm based 2-fold change ratio >1.5, 12 of them encoded secreted proteins (5-fold enrichment). Table 1B below lists the detailed expression information about 38 out of these 50 genes, excluding 12 unknowns. Log 2FC represents absolute log 2 value of fold change when type VI value was compared to type I and III values. Adjusted p values were calculated using the Benjamini and Hochberg (BH) method. The full microarray database is available at GEO (GSE22022) which is hereby incorporated by reference as available on Jun. 23, 2010 (this will be the day that we submit the patent application).

TABLE 1B

Regulated Genes in Fibroblasts Derived from Different Skin Phenotypes

| Name | Median (log2 ratio) I | III | VI | log2(FC) | P value | Adjusted P value | Secreted Protein |
|---|---|---|---|---|---|---|---|
| UP-REGULATED | | | | | | | |
| KRTHA4—Keratin, hair, acidic, 4 | 1.30925 | 0.95715 | 3.86629 | 2.71 | 0.00003 | 0.41325 | |
| CRYBB2—Crystallin, β B2 | −1.32113 | −0.30194 | 1.22988 | 2.25 | 0.00005 | 0.41325 | |
| EFNA1—Ephrin-A1 | −4.37199 | −4.21421 | −1.43136 | 2.02 | 0.00005 | 0.41325 | yes |
| GSTT2—Glutathione S-transferase theta 2 | −0.16210 | 0.11467 | 2.62813 | 2.40 | 0.00067 | 0.91936 | |
| TFPI2—Tissue factor pathway inhibitor 2 | −0.71547 | −0.59174 | 0.69919 | 1.70 | 0.00139 | 0.97624 | yes |
| BTRC—β-transducin repeat containing | 0.15708 | 0.15608 | 1.10714 | 1.55 | 0.00335 | 0.97624 | |
| NRG 1—Neuregulin 1 | 2.46678 | 1.78637 | 3.99343 | 1.55 | 0.00381 | 0.97624 | yes |
| HCLS1—Hematopoietic cell-specific Lyn substrate 1 | −1.49597 | −1.21545 | −0.02273 | 1.51 | 0.00629 | 0.97624 | |
| UPF2—UPF2 regulator of nonsense transcripts homolog (yeast) | 1.01005 | 1.19935 | 1.82232 | 1.57 | 0.00971 | 0.97624 | |
| GSTM1—Glutathione S-transferase M1 | −2.22740 | 1.22745 | 0.93667 | 2.54 | 0.01007 | 0.97624 | |
| CMAH—Cytidine monophosphate-n-acetylneuraminic acid hydroxylase | 0.97859 | 1.91148 | 3.08292 | 1.78 | 0.01313 | 0.97624 | |
| GALNAC4S-6ST—B cell RAG associated protein | −2.07167 | −2.34407 | −0.41729 | 1.86 | 0.01905 | 0.97624 | |
| NEURON NAVIGATOR 1; Pore membrane and/or filament interacting like protein 3; steerin-1 | 2.82948 | 2.59106 | 3.90176 | 1.79 | 0.02646 | 0.97624 | |
| LCP2—Lymphocyte cytosolic protein 2 (SH2 domain containing leukocyte protein of 76 kDa) | −2.67945 | −2.04973 | −1.92174 | 1.70 | 0.02793 | 0.97624 | |
| TGM2—Transglutaminase 2 (C polypeptide, protein-glutamine-γ-glutamyltransferase) | −0.58623 | −0.94246 | 1.77969 | 1.63 | 0.04069 | 0.97624 | |
| MPHOSPH1—M-phase phosphoprotein 1 | −1.96675 | −2.20821 | −1.33478 | 1.56 | 0.04926 | 0.97624 | |
| DOWN-REGULATED | | | | | | | |
| RPS23—Ribosomal protein S23 | 1.49350 | 1.80052 | −0.24952 | −1.78 | 0.00010 | 0.44627 | |
| PSG5—Pregnancy specific P-1-glycoprotein 5 | 5.60746 | 5.74012 | 3.41874 | −1.80 | 0.00082 | 0.91936 | yes |
| RAB38—RAB38, member RAS oncogene family | −1.08797 | −2.01221 | −3.28634 | −1.70 | 0.00153 | 0.97624 | |
| COLEC12—Collectin sub-family member 12 | 1.72114 | 1.59593 | −1.00132 | −2.03 | 0.00167 | 0.97624 | |
| MME—Membrane metallo-endopeptidase (neutral endopeptidase. enkephalinase, CALLA, CD 10) | 5.00920 | 5.41872 | 3.58369 | −1.78 | 0.00213 | 0.97624 | |
| CXorf1 O—Hypothetical gene supported by AK057608 | 1.42488 | 1.37446 | −0.00006 | −1.55 | 0.00272 | 0.97624 | |
| FLB0834—Hypothetical protein FLJ30834 | 3.43579 | 3.77251 | 1.27469 | −1.99 | 0.00297 | 0.97624 | yes |
| ALDH1A1—Aldehyde dehydrogenase 1 family, member A1 | 0.49772 | 0.30924 | −1.66049 | −1.67 | 0.00311 | 0.97624 | |
| SLC40A1—Solute carrier family 40 (iron-regulated transporter), member 1 | 0.24879 | −0.60968 | −2.49485 | −1.90 | 0.00331 | 0.97624 | |
| RLN2—Relaxin 2 (H2) | 0.52112 | 1.65270 | −0.51706 | −1.72 | 0.00392 | 0.97624 | yes |
| APOD—Apolipoprotein D | 0.79302 | 0.89137 | −1.13356 | −1.61 | 0.00580 | 0.97624 | |
| G2SYN—Gamma-2-syntrophin (syntrophin 5) (syn5) | 1.11616 | 1.40465 | 0.43173 | −1.54 | 0.00748 | 0.97624 | |
| PDGFD—DNA-damage inducible protein 1 | 2.94860 | 3.10007 | 1.82904 | −1.74 | 0.00954 | 0.97624 | yes |
| PSG5—Pregnancy specific P-1-glycoprotein 5 | 6.18731 | 6.03234 | 4.49127 | −2.12 | 0.01061 | 0.97624 | yes |
| DAB 1—Disabled homolog 1 (Drosophila) | 2.42132 | 2.24755 | 1.15194 | −1.85 | 0.01102 | 0.97624 | |
| GAS 1—Growth arrest-specific 1 | 4.22178 | 2.90260 | 1.90995 | −1.54 | 0.01188 | 0.97624 | |
| FLJ25124—Hypothetical protein FLJ25124 | 3.55269 | 2.48627 | 1.66417 | −1.80 | 0.01266 | 0.97624 | |
| PDK4—Pyruvate dehydrogenase kinase, isoenzyme 4 | −1.31677 | −2.24754 | −3.17383 | −1.50 | 0.01675 | 0.97624 | |

TABLE 1B-continued

Regulated Genes in Fibroblasts Derived from Different Skin Phenotypes

| Name | Median (log2 ratio) | | | log2(FC) | P value | Adjusted P value | Secreted Protein |
|---|---|---|---|---|---|---|---|
| | I | III | VI | | | | |
| CD8B 1—CD8 antigen, βpolypeptide 1 (P37) | −2.37449 | −2.60499 | −4.62084 | −2.68 | 0.02095 | 0.97624 | yes |
| CYP4F3—Cytochrome P450, family 4, subfamily F, polypeptide 3 | −1.29395 | −0.11202 | −1.88195 | −2.00 | 0.02335 | 0.97624 | |
| SFRP1—Secreted frizzled-related protein 1 | 1.94190 | 1.72905 | −0.54364 | −1.54 | 0.02615 | 0.97624 | yes |
| Mitochondrial gtp binding protein isoform V | −0.12940 | 0.04256 | −1.59999 | −1.53 | 0.03140 | 0.97624 | |
| PSG3—Pregnancy specific β-1-glycoprotein 3 | 5.69948 | 5.18387 | 2.87082 | −1.75 | 0.03547 | 0.97624 | yes |
| CDNA FLJ40807 fis, clone TRACH2009268 | −1.00555 | −1.68502 | −2.75602 | −1.55 | 0.03941 | 0.97624 | |
| LIN28—Lin-28 homolog (C. elegans) | −5.17633 | −4.00111 | −6.01146 | −1.50 | 0.04196 | 0.97624 | |
| PSBG-11—Pregnancy-specific β1-glycoprotein 11 precursor | 2.74972 | 0.29803 | −0.88769 | −1.70 | 0.04940 | 0.97624 | yes |

Example 5

Expression of NRG-1 in Normal Human Skin and in Cultured Normal Human Fibroblasts This example illustrates expression of NRG-1 in normal human skin and in cultured normal human fibroblasts.

Among the 12 secreted genes that were differentially regulated in fibroblasts from skin type VI compared to skin types I and III (as noted in Table 1B), NRG-1 was one of the most highly up-regulated in fibroblasts derived from type VI skin. To validate the expression of NRG-1 by fibroblasts at the protein level, immunohistochemistry was performed to examine the expression of NRG-1 in normal human skin samples from types I and VI skin (FIG. 2A). NRG-1 was found to be highly expressed throughout the epidermis as well as in the dermis of type VI skin, but there was no significant expression of NRG-1 in the epidermis and only a very low level of NRG-1 expression in the dermis of type I skin. When fibroblasts derived from skin types I and VI were immunohistochemically stained for NRG-1 (FIG. 2B) using two different antibodies, both of them detected high levels of NRG-1 in most fibroblasts from the type VI skin both in the cytoplasm and in the nuclei whereas fibroblasts from type I skin showed very low levels of NRG-1 expression and only in a few cells. Western blotting of NRG-1 in the cell extracts showed that the 60-kDa isoform of NRG-1 is only expressed in fibroblasts derived from type VI skin, but not in fibroblasts derived from type I or III skin (FIG. 2C).

The expression of 3 other secreted proteins identified in the microarray analysis (PEDF, TIMP3 and calnexin) were characterized, but none of them showed any difference in expression that correlated with skin type.

Example 6

Effect of NRG-1 on the Pigmentation of 3-D Reconstructed Skin

This example illustrates the effect of NRG-1 on the pigmentation of three-dimensional (3-D) reconstructed skin.

Figure 3B:
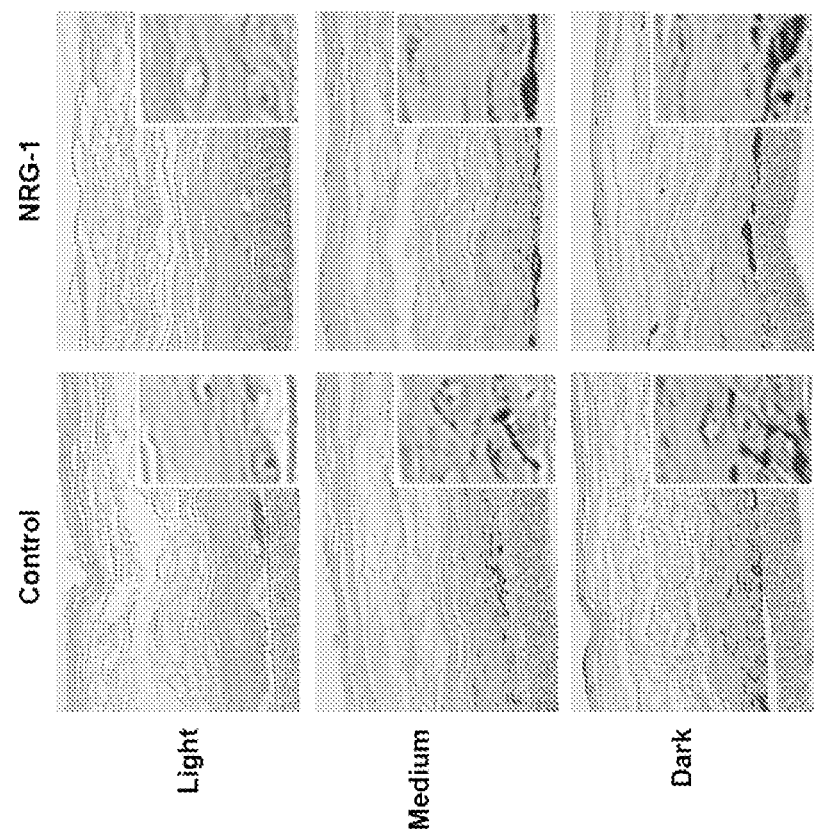
FIGS. 3A-3C are digital images illustrating the effect of NRG-1 on the pigmentation of 3-D reconstructed skins.
Figure 3A:
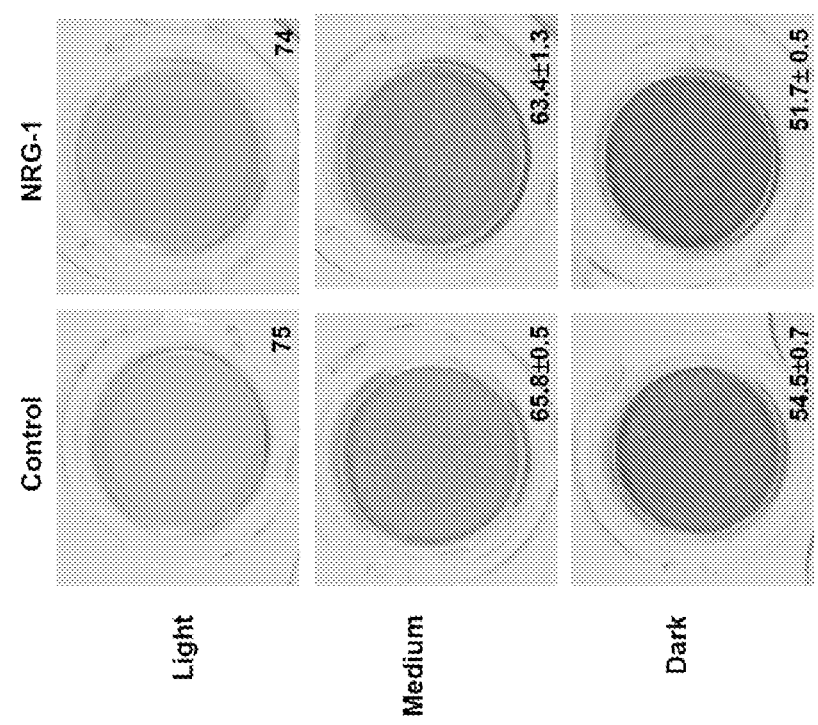
Figure 3C:
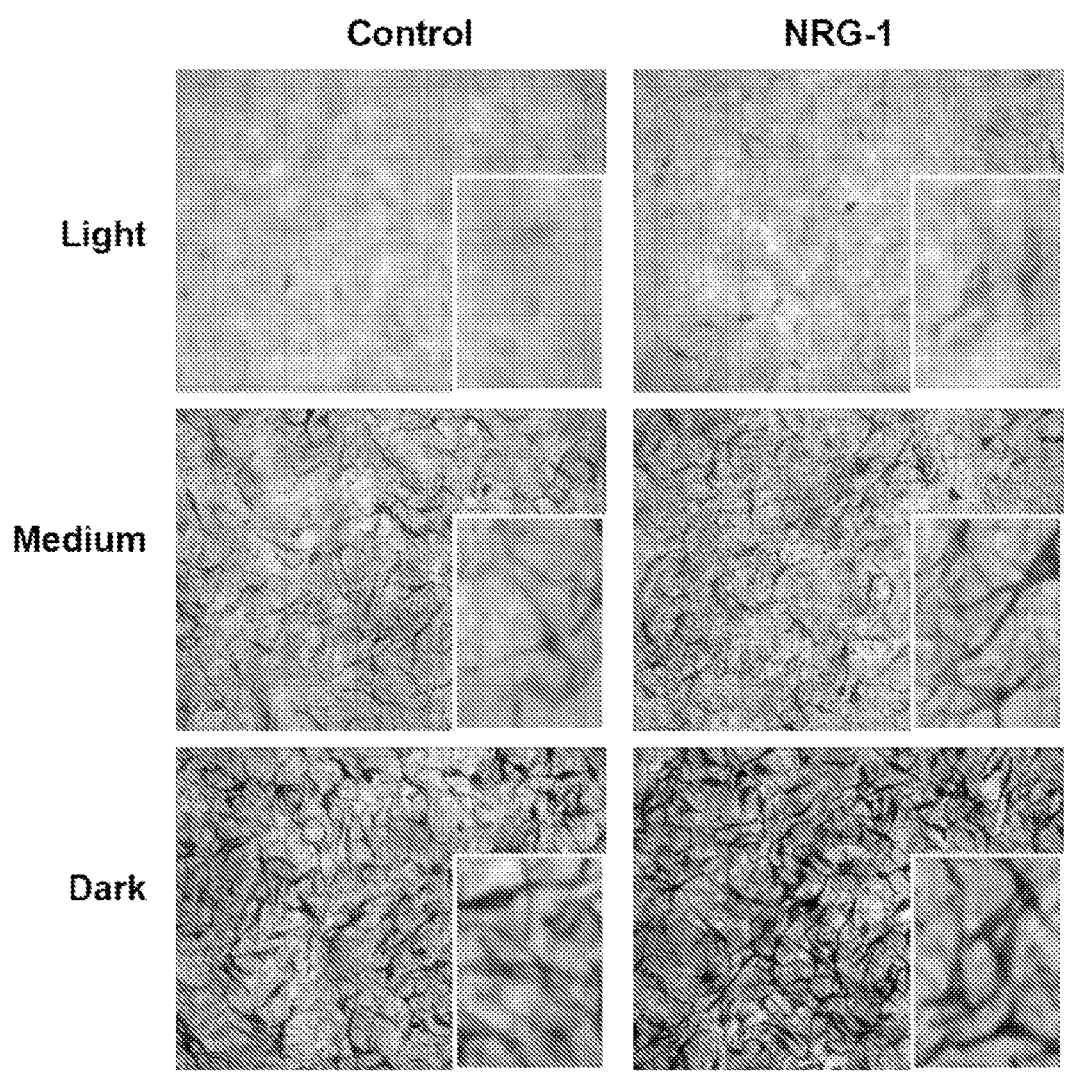
Figure 10:
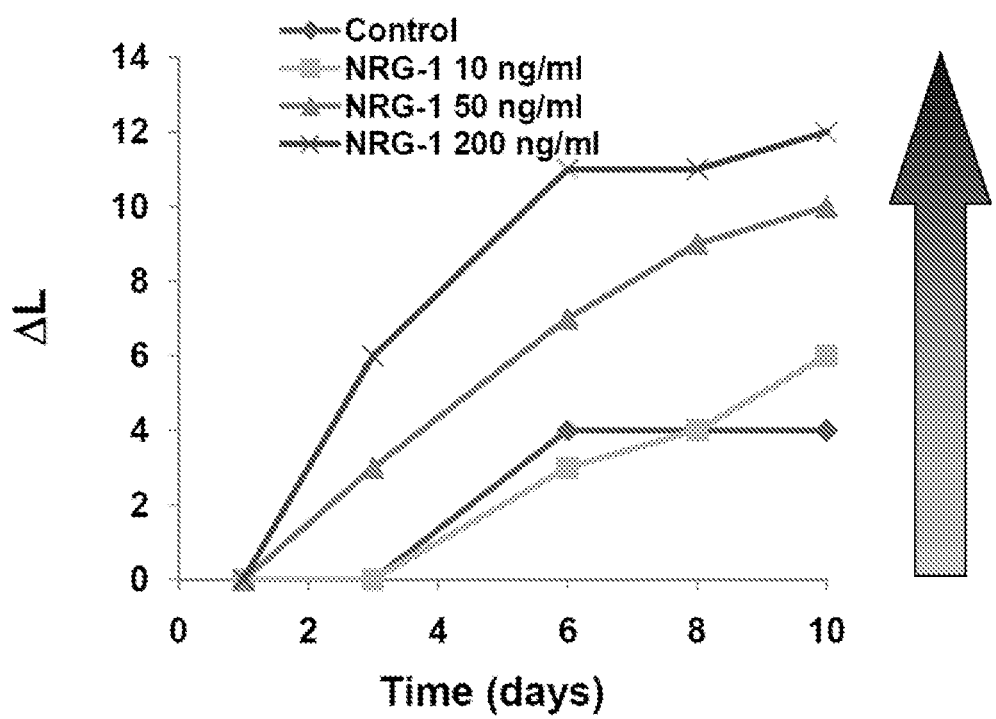
FIG. 10 is a graph illustrating the dose-response relationship of NRG-1 treatment on MelanoDerms. Medium (from Asian skin) MelanoDerms were treated with various concentrations of NRG-1 (from 10 to 200 ng/ml) for 10 days and the absolute ΔL values compared to Day 1 were plotted for each data point.
Figure 11:
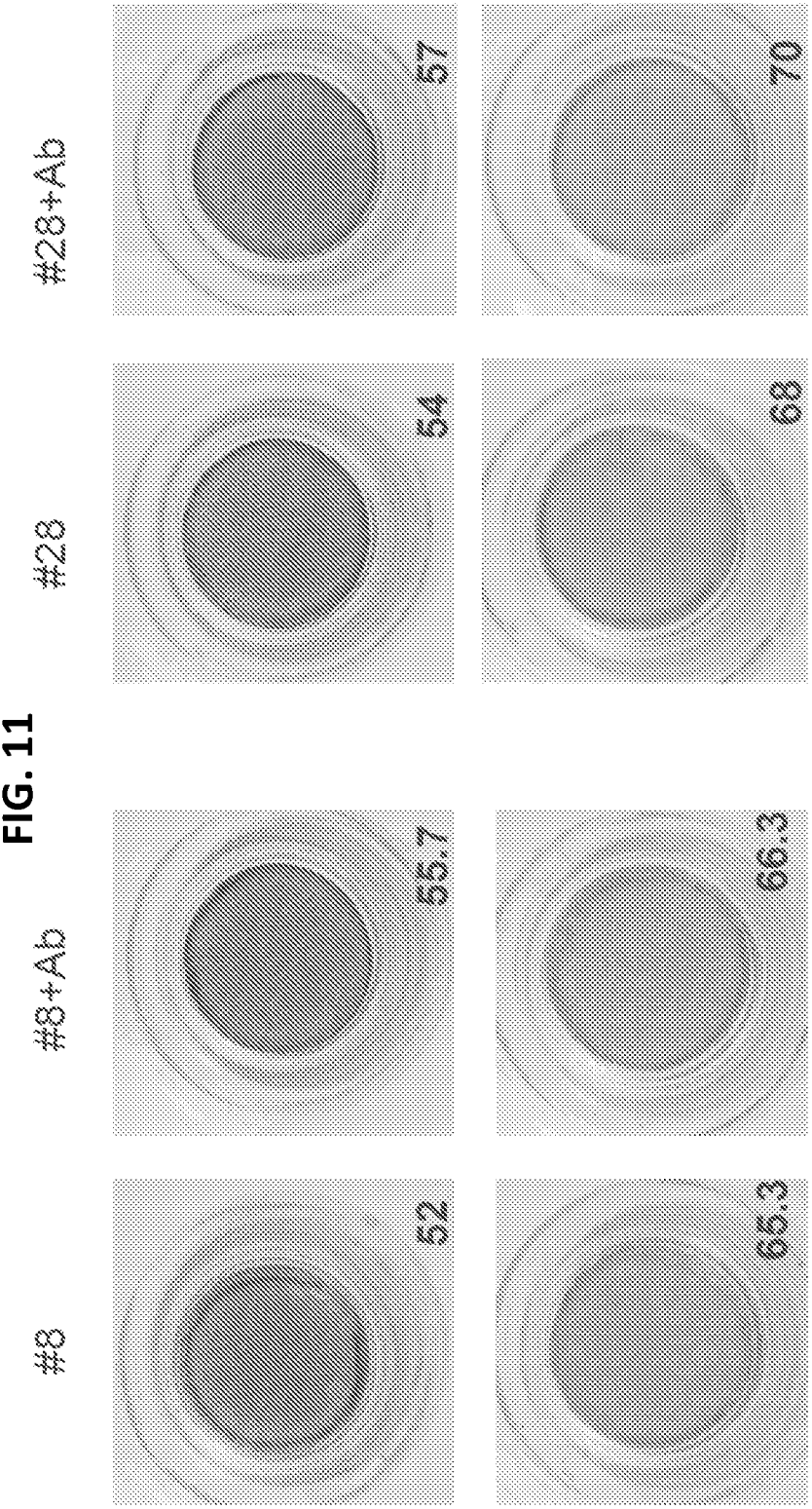
FIG. 11 is a series of digital images illustrating Melano-Derms treated with NRG-1 neutralizing antibody. NRG-1 neutralizing antibody (5 µg/ml) (R&D systems, $ND_{50}$=0.5~2 µg/ml) was used to see if it was able to block the action of NRG-1 from fibroblasts. Two fibroblast lines from type VI skin (#8 and 28) were co-cultured with Black or Asian MelanoDerms. MelanoDerms in the presence of NRG-1 neutralizing antibody or vehicle (PBS) alone are shown. Antibody decreased the pigmentation in both Black and Asian MelanoDerms.

Three dimensional (3-D) reconstructed human skin models (termed MelanoDerms) were used to test the effects of NRG-1 on skin pigmentation. Three types of MelanoDerm, 'light' (from Caucasian skin), 'medium' (from Asian skin) and 'dark' (from African-American skin), were used to compare the effects of NRG-1 on those three types of skin. In preliminary studies to optimize the concentration of NRG-1 (from 10 to 200 ng/ml were tested, FIG. 10), 50 ng/ml was chosen which was consistent with concentrations of NRG-1 used for other cell types by other groups. NRG-1 was added to the MelanoDerm media at 50 ng/ml and the medium was replenished every 2 days. On day 9, the MelanoDerms treated with NRG-1 were compared to controls treated only with vehicle. Pigmentation of the skin was assessed using the L value, higher L values indicating lighter colors. The dark MelanoDerms treated with NRG-1 showed increases in pigmentation ($\Delta L=-3$) (FIG. 3A), whereas the effects of NRG-1 on the medium and light MelanoDerms were less, although increases in pigmentation occurred ($\Delta L=-2$ and $-1$, respectively). It should be noted that relatively small changes in $\Delta L$ can represent relatively large changes in visible skin color. For example, the mean L value of White/Caucasian skin is 67, that of Asians, Pacific-Islanders is 65, that of Hispanic/Latinos is 64, and that of American Indian/Alaska Native is 62. Cross-sections of those tissues revealed that most of the melanin pigment in the NRG-1 treated MelanoDerms resided in the basal layer of the epidermis, and had particularly accumulated around the melanocytes (FIG. 3B). In the vehicle-treated control MelanoDerms, melanin pigment was more evenly distributed throughout the entire epidermis and no visible melanin accumulation was observed around melanocytes (FIG. 3B). When melanocyte morphology was examined using bright field microscopy, MelanoDerms treated with NRG-1 showed more abundant cytoplasm with thicker dendrites compared to the vehicle-treated control Melano-Derms (FIG. 3C). Therefore, NRG-1 leads to visible increases in pigmentation in the MelanoDerms which was greater as the skin had more constitutive pigmentation.

Figure 4C:
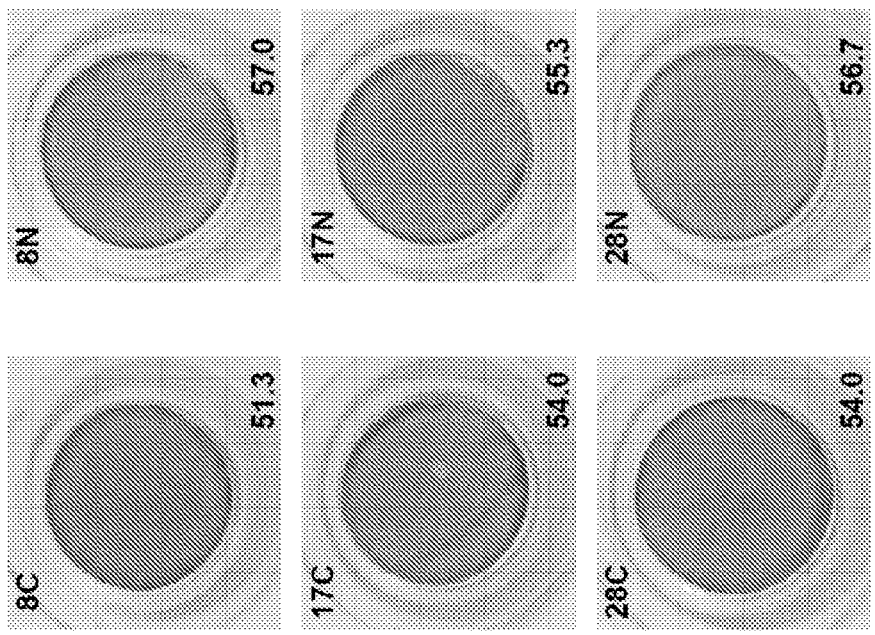
FIGS. 4A-4C are digital images illustrating the effect of NRG-1 knock-down by shRNA transduction.
Figure 4A:
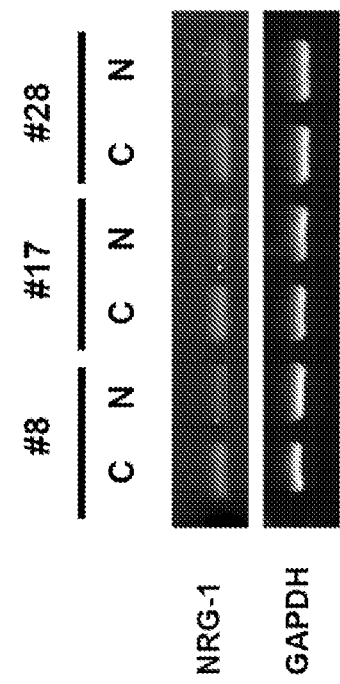
Figure 4B:
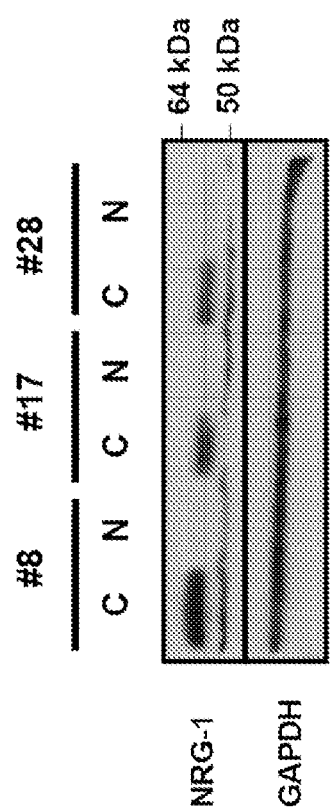

The effect of NRG-1 knock-down in fibroblasts derived from type VI skin was examined using shRNA transduction. FIG. 4A shows that NRG-1 mRNA was decreased significantly by the NRG-1 shRNA, and FIG. 4B shows that 60-kDa NRG-1 protein, which is only expressed in fibroblasts derived from type VI skin (FIG. 2C), was successfully knocked-down as well. When dark MelanoDerms were co-cultured with fibroblasts with knock-down of NRG-1, the pigmentation level was significantly lower than MelanoDerms co-cultured with fibroblasts transduced with control shRNA (FIG. 4C). These results further support that NRG-1 secreted from fibroblasts derived from type VI skin regulates the constitutive level of pigmentation in type VI skin. These studies also indicate that MelanoDerms can be used as an in vivo model to study the effects of NRG-1 modulators on skin pigmentation levels.

Example 7

Effect of NRG-1 on the Proliferation and Pigmentation of Human Melanocytes

This example illustrates the effect of NRG-1 on the proliferation and pigmentation of human melanocytes.

The effects of NRG-1 on the proliferation of human melanocytes derived from light skin (HEM-LP) as well as those derived from dark skin (HEM-DP) were used to compare the effects of NRG-1 on different types of melanocytes. When NRG-1 (50 ng/ml) was added to the melanocyte medium, cell numbers were significantly higher as early as day 1 both for HEM-LP and for HEM-DP melanocytes and that increase continued until they become fully confluent (FIG. 5A, 5B). The PI-3K-Akt pathway is one of the pathways to be involved in NRG-1-mediated effects on proliferation. Therefore, the phosphorylation level of Akt was examined in NRG-1 treated melanocytes compared to controls. In both HEM-LP and HEM-DP melanocytes, levels of p-Akt were significantly higher in NRG-1-treated cells on day 5 (FIG. 5C). Next, the time course of p-Akt levels after treatment with NRG-1 were examined. Levels of p-Akt were equally high in the NRG-1 treated HEM-DP melanocytes and in the control cells on day 1 when the cells were at a low confluency (~15%). However, the level of p-Akt had significantly decreased in the control by day 3, while the NRG-1-treated cells maintained higher levels of p-Akt through day 5 (FIG. 5D).

Figure 6A:
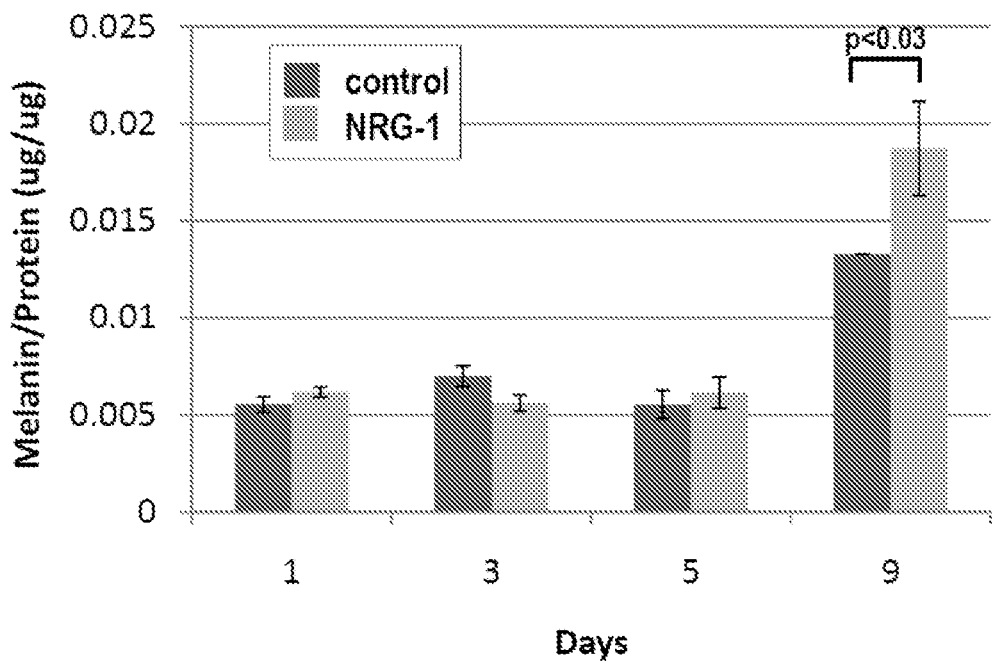
FIGS. 6A and 6B are bar graphs illustrating the effect of NRG-1 on the pigmentation of cultured human melanocytes.
Figure 6B:
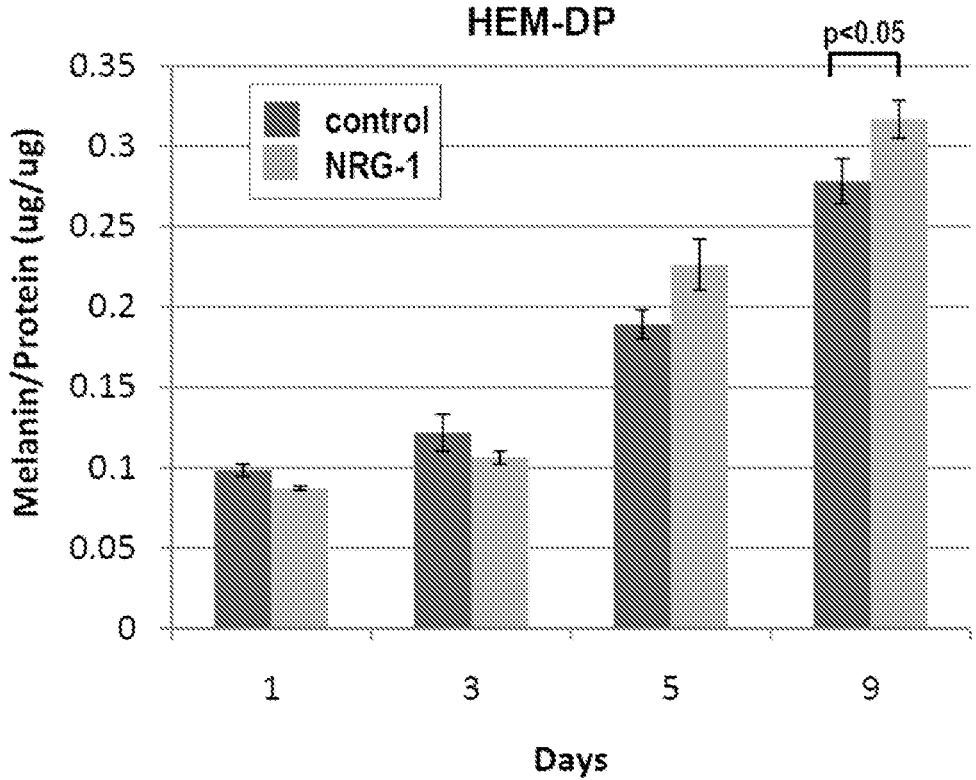

The effects of NRG-1 on the pigmentation of human melanocytes were also examined. In lightly pigmented HEM-LP melanocytes, the level of pigmentation (melanin/protein) was not significantly different between the NRG-1-treated cells and the control cells from days 1 through 5 when the cells were subconfluent and were still actively proliferating. However, on day 9, when the cells had reached confluence, the pigmentation level of NRG-1-treated HEM-LP melanocytes was about 35% higher than the control (FIG. 6A). In the darkly pigmented HEM-DP melanocytes, the pigmentation level of NRG-1-treated cells was higher than the controls starting at day 5 (FIG. 6B) when the cells were still subconfluent and remained higher at day 9.

Example 8

NRG-1 Receptors Expressed by Human Melanocytes

This example illustrates expression of NRG-1 receptors, including ERBB2, ERBB3 and ERBB4 on human melanocytes.

Figure 7B:
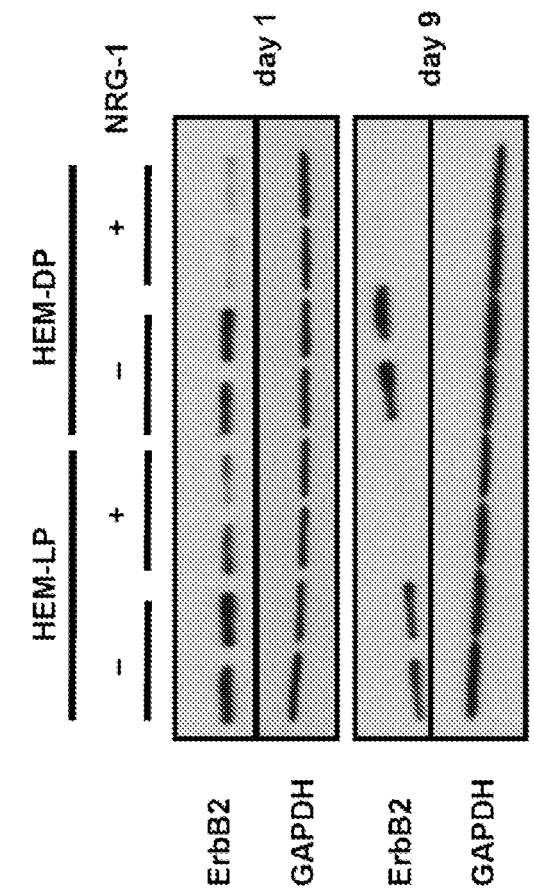
FIGS. 7A and 7B are digital images illustrating expression of ERBBs after NRG-1 treatment.
Figure 7A:
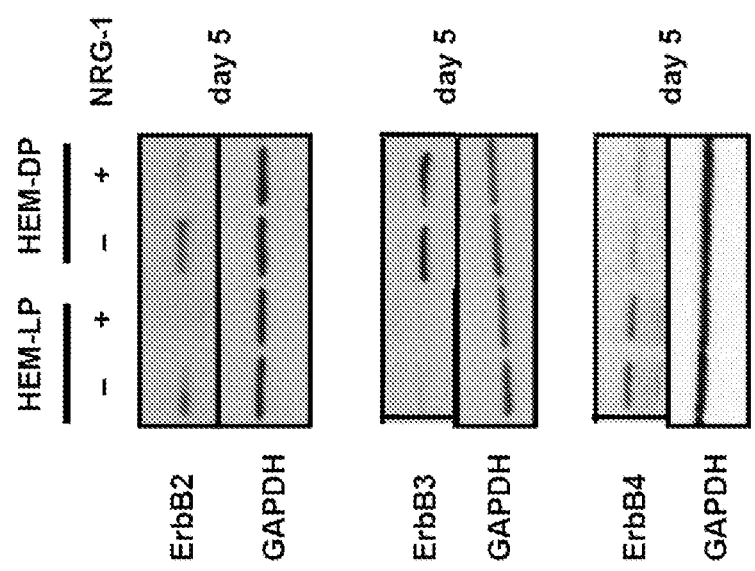

NRG-1 is a ligand for the EGFR family receptors, ERBB3 and ERBB4. EGFR (ERBB1) is not expressed by human melanocytes and NRG-1 cannot directly bind to ERBB2. Thus, the levels of ERBB3 and ERBB4 (as well as ERBB2) in HEM-LP and in HEM-DP melanocytes were examined. ERBB3 is highly expressed by HEM-DP melanocytes and its expression level was not affected by treatment with NRG-1 (FIG. 7A). In contrast, only trace levels of ERBB3 were detected in HEM-LP melanocytes and there was no detectable change in that expression elicited by NRG-1. ERBB4 was highly expressed in the lightly pigmented HEM-LP melanocytes, but its expression level was very low in the darkly pigmented HEM-DP melanocytes (FIG. 7A). Levels of ERBB4 expression also did not change after treatment with NRG-1. Interestingly, the expression of ERBB2, a co-receptor for NRG-1 signaling, which was similarly expressed in untreated controls of both types of melanocytes, was almost completely undetectable after 5 days of treatment with NRG-1 both in HEM-LP and in HEM-DP melanocytes. The time course of effects of NRG-1 on ERBB2 expression was examined in more detail. Only 1 day of treatment with NRG-1 was sufficient to significantly decrease the level of ERBB2 in both types of melanocytes (FIG. 7B), and ERBB2 expression had completely disappeared by day 3. This effect lasted until day 9 when the cells were almost 100% confluent.

Whether the decrease in ERBB2 level elicited by NRG-1 was due to transcriptional regulation or to proteasomal degradation was further explored. When ERBB2 mRNA levels were measured after 1 day of treatment with NRG-1, NRG-1 treated cells and controls were similar both for HEM-LP and for HEM-DP melanocytes (FIG. 8A) despite the marked decrease in ERBB2 protein expression noted above. When the cells were treated with NRG-1 together with MG132 (120 nM), which inhibits proteasomal function, the level of ERBB2 protein returned to the control level, which indicates that NRG-1 promotes the proteasomal degradation of ERBB2 (FIG. 8B).

Figure 9A:
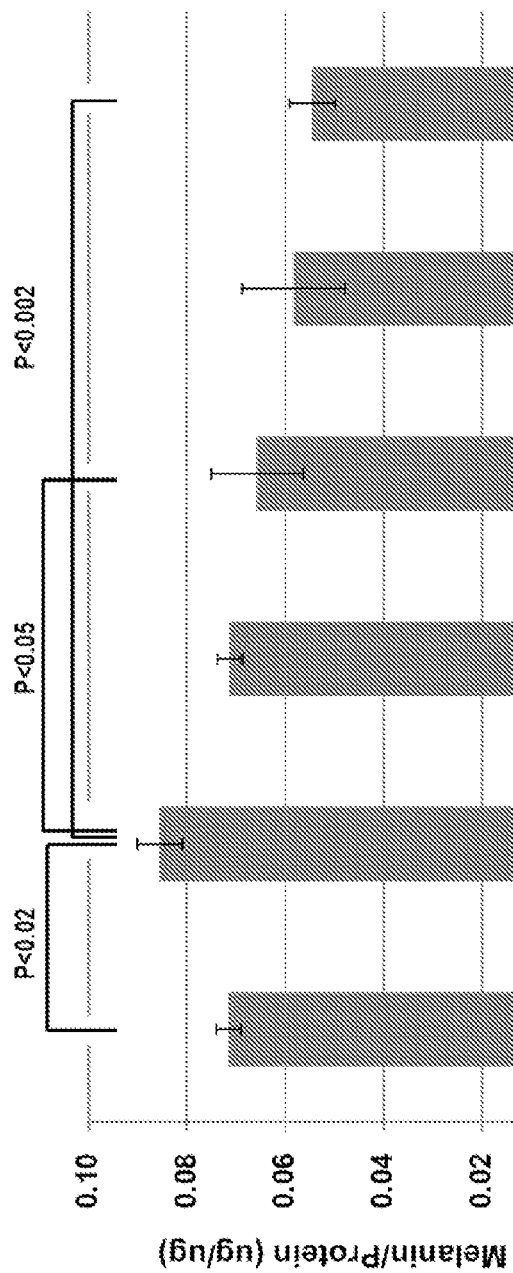
FIGS. 9A and 9B are digital images illustrating the effect of pan-ERBB inhibitors on NRG-1 action on human melanocytes and MelanoDerms.
Figure 9B:
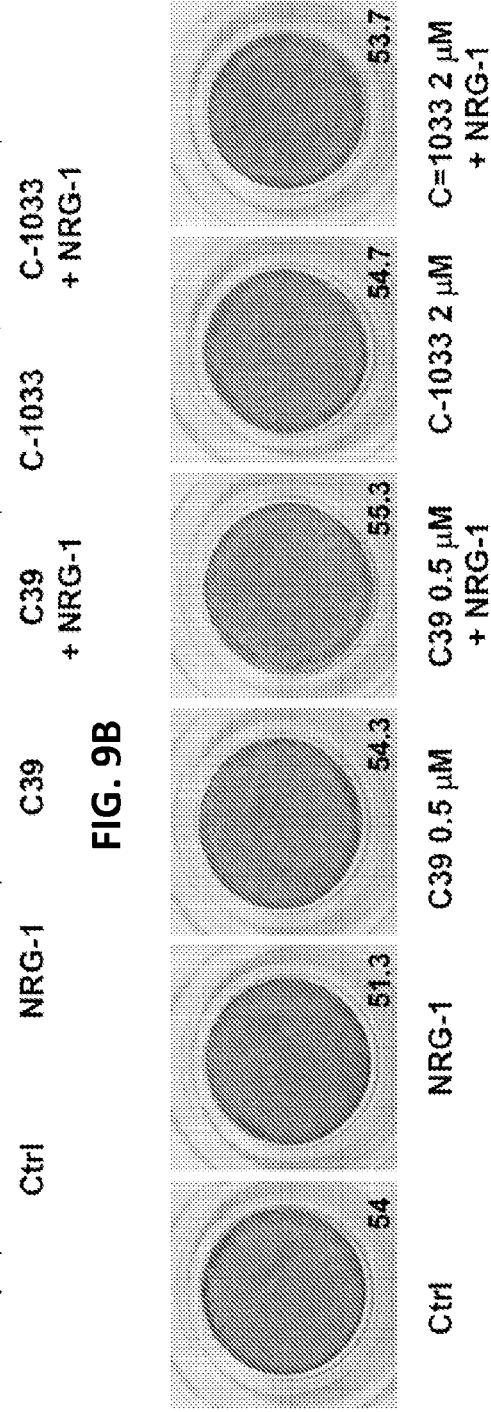

Finally, to confirm the involvement of ERBB receptors in the action of NRG-1, two different pan-ERBB inhibitors (C39 and CI-1033) were used to see if they would reverse the effect of NRG-1 in HEM-DP melanocytes and/or in dark MelanoDerms. C39 (0.5 µM) or CI-1033 (2 µM) alone did not affect the melanin content of HEM-DP melanocytes, while NRG-1 alone stimulated melanin content as expected (FIG. 9). However, when cells were treated with NRG-1 in the presence of either ERBB inhibitor, the melanin content remained at the same level as the control. Similarly, when dark MelanoDerms were treated with either of those ERBB inhibitors, NRG-1 treatment did not increase the pigmentation of MelanoDerms compared to the control. Therefore, these studies indicate that ERBB receptors are involved in the action of NRG-1 on melanocytes.

Once NRG-1 binds to ERBB3 or ERBB4, it can produce ERBB3/ERBB2 or ERBB4/ERBB2 heterodimers or ERBB4 homodimers to initiate the downstream signaling. Receptor dimerization leads to the activation of intracellular signaling pathways that include phosphatidylinositol-3-kinase (PI-3K) and the mitogen activated protein kinase (MAPK) pathways.

The present results show that NRG-1 increases the proliferation of human melanocytes possibly via the phosphorylation of Akt, and that it increases pigmentation levels in the MelanoDerm skin model and in cultured human melanocytes. One aspect of the disclosed studies is that NRG-1 is much more efficient in increasing melanin content as the melanocytes became confluent. Therefore, it seems that the initial effect of NRG-1 is to increase proliferation, and then to increase pigmentation when proliferation becomes limiting. In the MelanoDerm skin model, NRG-1 did not increase melanocyte growth, but it did increase the size of melanocytes accompanied by an accumulation of melanin pigments and also increased the thickness of dendrites and/or degree of dendricity of melanocytes in the basal layer. This might be closer to the physiological situation where the number of melanocytes in lighter and in darker skin is comparable and melanocytes do not usually proliferate unless there is a strong stimulatory signal such as UV. Therefore, it is possible that NRG-1 affects the dendricity and pigment synthesis of melanocytes and the distribution of melanin in human skin.

NRG-1 binds to ERBB3 or ERBB4 which in turn can form heterodimers with ERBB2 or can form homodimers by themselves (such as ERBB4-ERBB4) to activate downstream signaling. When melanocyte cultures or MelanoDerms were treated with pan-ERBB inhibitors, they were able to prevent the effects of NRG-1. Under normal conditions, ERBB3 was highly expressed only in HEM-DP melanocytes, whereas ERBB4 was highly expressed only in HEM-LP melanocytes. Therefore, the different levels of ERBB3 and ERBB4 receptors in the HEM-LP and HEM-DP melanocytes could explain why the effect of NRG-1 was more evident in dark MelanoDerms and in darkly pigmented HEM-DP melanocytes than in light MelanoDerms and in lightly pigmented HEM-LP melanocytes. Other mechanisms/factors unique to melanocytes from dark skin may function together with NRG-1 for synergistic effects on melanogenesis.

ERBB2 is an oncogene, which is constitutively activated in melanoma cells and in some other types of cancer cells. NRG-1 cannot bind to ERBB2 directly, but it may augment ERBB receptor signaling by acting as an auxiliary co-receptor. One of the findings of the present study is that NRG-1 ligand binding leads to the complete abrogation of ERBB2 receptor levels due to increased proteasomal degradation both in HEM-LP and in HEM-DP melanocytes. This finding indicates that targeting ERBB2 could be an effective strategy for melanoma prevention or intervention.

Overall, these studies provide a database of potential novel melanogenic factors that regulate the constitutive pigmentation of different phenotypes of human skin and can such factors can serve as potential therapeutic targets to prevent or treat melanomas.

Example 9

Method of Identifying NRG-1 Bioactive Fragments

This example illustrates a method of identifying NRG-1 bioactive fragments for use of modulating NRG-1 activity, such as to prevent or treat a skin disorder.

Peptides ranging from 7 to 15 amino acids in length are synthesized and purified from the 8 kDa NRG-1 (amino acids 176-256 of SEQ ID NO: 7) according to techniques known to those of skill in the art. The effects of the synthesized peptides on melanocyte pigmentation and proliferation is evaluated in the MelanoDerm human skin model (as described in detail in Example 6) or on human skin grafts on a nude mouse model as previously described by Petersen et al., *J. Clin. Invest.* 74: 1358-1365, 1984; this reference is hereby incorporated by reference in its entirety.

For the human skin grafts, full-thickness human face skin is grafted onto 60 adult male nude mice. 4 weeks after grafting the mice are divided into the following groups: control (5 animals); vehicle (5 animals), and 50 NRG-1 treated animals (further sub-divided into groups of 5 to allow 10 different synthesized NRG-1 fragments to be tested). NRG-1 treated animals receive 50 ng/ml of the test peptide, by topical administration daily. After 10 days of treatment, the skin grafts treated with NRG-1 are compared to control (graft treated with no compound) or vehicle by use of bright field microscopy. A bioactive NRG-1 fragment is one that resulted in a visually apparent increase in dendrite thickness and cytoplasm abundance as compared to vehicle-treated or control skin grafts.

The effect of NRG-1 bioactive fragments on proliferation is determined by seeding melanocytes (e.g., A375 or SK23 cells) in triplicate at 1000 cells/well. Cells are cultured for at least 8 days in medium with or without 50 ng/ml of the various NRG-1 bioactive fragments. After 10 to 15 days, the clones are fixed and stained with crystal violet. Proliferation is measured according to optical density (Passeron et al. *Proc. Natl. Acad. Sci. USA*, 104:13984-13989, 2007). A two-fold increase in melanocyte proliferation is indicative of an NRG-1 fragment that is effective at increasing melanocyte proliferation.

Example 10

NRG-1 Peptide Fragments Increase Melanocyte Pigmentation

This example demonstrates the ability of specific NRG-1 peptides to increase pigmentation in human epidermal melanocytes.

Figure 13:
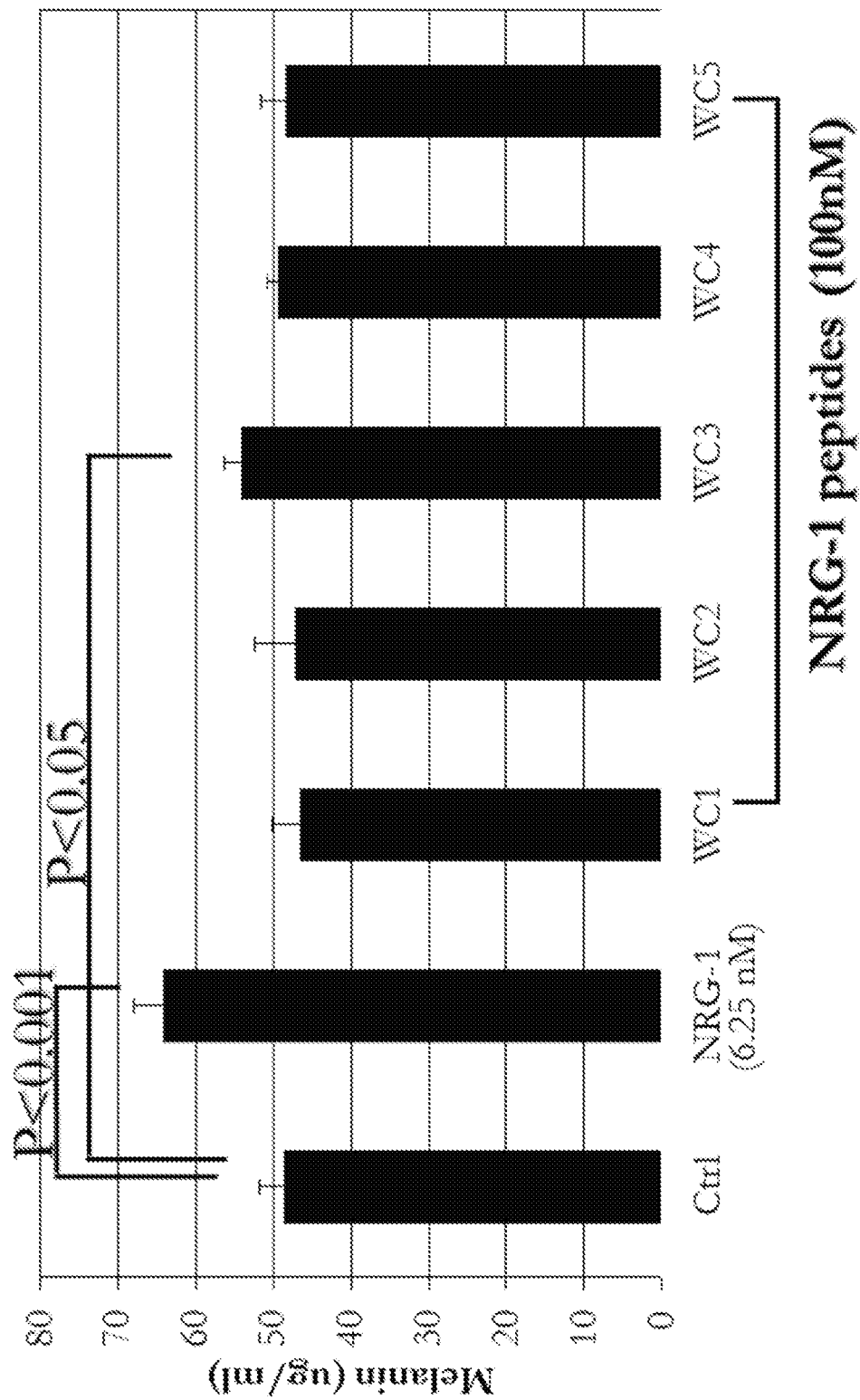
FIG. 13 is a bar graph demonstrating increased pigmentation in darkly-pigmented human epidermal melanocytes (HEM-DP) with each of the 16-mer peptides (100 nM) or the commercially available rhNRG-1 (6.25 nM) or the vehicle only (0.1% BSA in PBS) every other day for 7 days. WC-03 resulted in the highest melanin increase compared to the control (n=4).

The EGF domain of NRG-1 can activate the NRG-1 receptors. Two exemplary EGF domains of NRG-1 were aligned (SEQ ID NOs: 9 and 10) and 5 different 16-mer peptides within these two sequences were designed (FIG. 12). Darkly-pigmented human epidermal melanocytes (HEM-DP) were treated with each of the 16-mer peptides (100 nM) or the commercially available rhNRG-1 (6.25 nM) or the vehicle only (0.1% BSA in PBS) every other day for 7 days. As illustrated in FIG. 13, WC-03 showed the highest increase in pigmentation compared to control.

Figure 14:
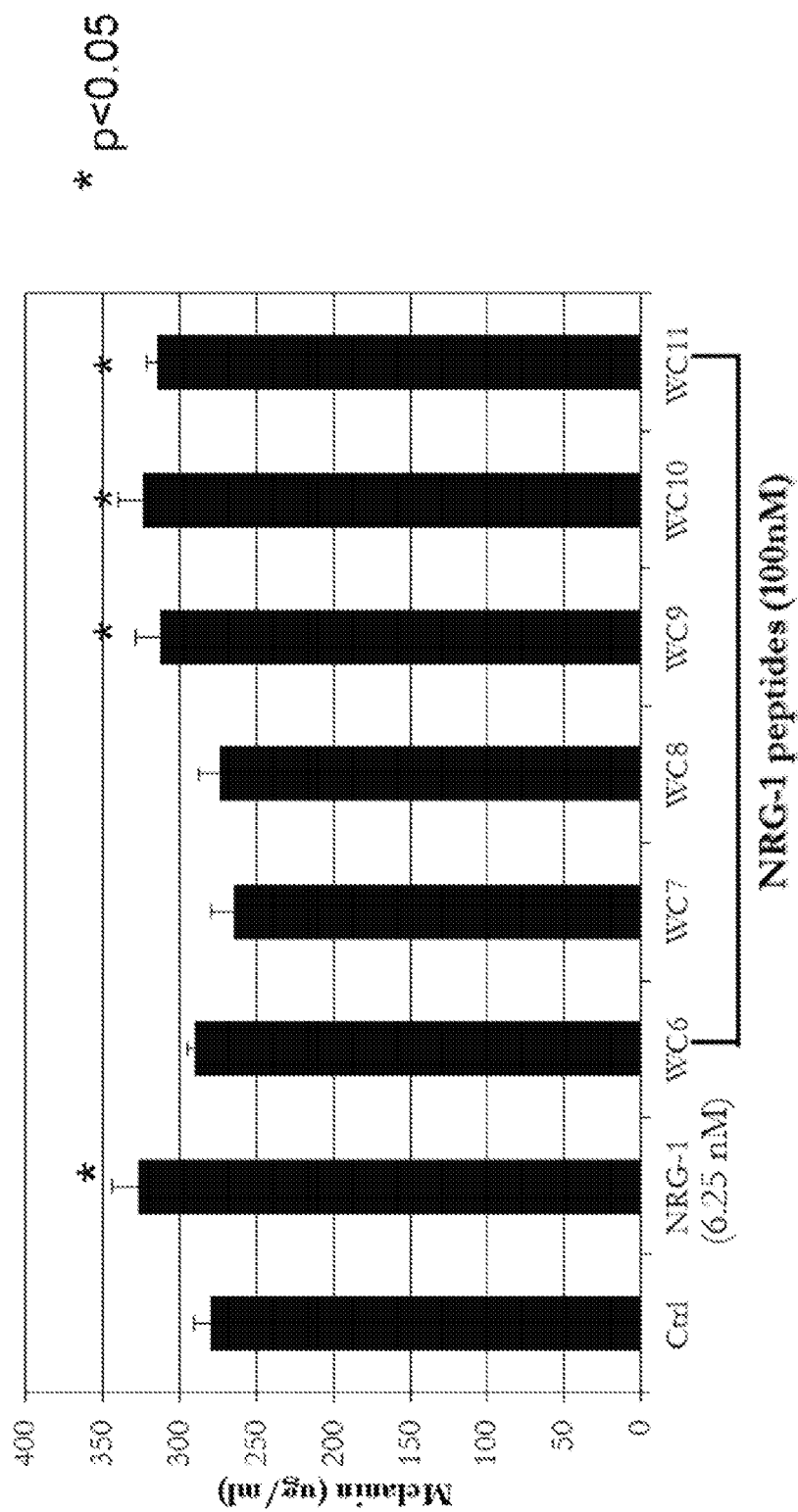
FIG. 14 is a bar graph demonstrating pigmentation levels in HEM-DP following administration of 8-mer NRG-1 peptides within the WC-03 region (WC6-WC10, 100 nM) or the full length EGF domain of NRG-1 (WC11, 100 nM) or the commercially available rhNRG-1 (6.25 nM) or vehicle only (0.1% BSA in PBS) every day for 9 days. WC9 and WC 10 caused statistically significant increases of pigmentation in HEM-DP.

Based on these results, 8-mer peptides within WC-03 region were designed and evaluated for altering pigmentation in HEM-DP. In particular, HEM-DP were treated with each of the 8-mer peptides (WC-6, GGECFMVK, amino acids 3-10 of SEQ ID NO: 10; WC-7, FMVKDLSN, amino acids 8-15 of SEQ ID NO: 10; WC-8, DLSNPSRY, amino acids 12-19 of SEQ ID NO: 10; WC-9, PSRYLCKC, amino acids 16-23 of SEQ ID NO: 10; WC-10, LCKCPNEF, amino acids 20-27 of SEQ ID NO: 10; 100 nM) or the full length EGF domain of NRG-1 (WC-11, SEQ ID NO: 10, 100 nM) or the commercially available rhNRG-1 (SEQ ID NO: 11, 6.25 nM) or vehicle only (0.1% BSA in PBS) every day for 9 days. As illustrated in FIG. 14, WC-9 and WC-10 induced statistically significant increases of pigmentation.

These studies indicate that specific NRG-1 peptides are capable of increasing pigmentation in HEM-DP.

Example 11

Method of Identifying a NRG-1 Bioactive Fragment Effective for Altering Skin Pigmentation or Preventing UV Skin Damage This example illustrates a method of identifying an NRG-1 bioactive fragment effective for altering skin pigmentation and/or for treatment for preventing UV skin damage in a human.

Full-thickness human face skin is grafted onto 60 adult male nude mice. 4 weeks after grafting the mice are divided into the following groups: control (5 mice, no UV exposure); UV only (5 mice), and 50 NRG-1 and UV treated mice (further sub-divided into groups of 5 to allow 10 different UV protocols to be evaluated). NRG-1 treated mice receive 50 ng/ml of the test peptide, by topical administration daily for 7 days prior to UV exposure of 1 minimal erythema dose (MED)). Immediately (approximately 7 minutes), 1 day or 7 days after UV exposure, the skin grafts treated with NRG-1 prior to UV exposure are compared to control (graft treated with no compound or UV) or UV alone, in which skin pigmentation in the various samples is measured by reflectance spectroscopy. A 20% increase in pigmentation indicates a composition effective for altering skin pigmentation and possibly for treating or preventing UV skin damage.

Whether the increase in pigmentation improved photoprotection is determined by subjecting the treated and untreated skin to a 1 MED UV (challenge at the end of the NRG-1 peptide treatment period), then taking a shave or punch biopsy, using immunohistochemistry to assess DNA damage due to the UV treatment by measuring DNA photoproducts (cyclobutane pyrimidine dimers (CPD) and (6-4) photoproducts (64PP), two major types of DNA lesions resulting from UV damage) with antibodies that specifically bind to CPD or 64PP. A 20% difference between DNA photoproducts detected in the NRG-1 treated and non-treated samples following UV treatment, in which the NRG-1 treated has approximately 20% less DNA photoproducts than the untreated samples, indicates improved photoprotection.

Example 12

Method of Identifying an NRG-1 Bioactive Fragment for Treating Melanoma

This example illustrates a method of identifying an NRG-1 bioactive fragment of an NRG-1 full length peptide for treating melanoma.

Human melanomas are grafted onto 15 adult male nude mice. 4 weeks after grafting the mice are divided into the following groups: control (5 mice, no compound exposure); vehicle only (5 mice), and 5 NRG-1 treated mice (50 ng/ml of NRG-1). NRG-1 treated mice receive 50 ng/ml of the NRG-1 test peptide, by topical administration daily for 30 days. Tumor diameter and mouse survival is monitored daily. A 10% reduction in tumor size as compared to control or vehicle indicates that the NRG-1 fragment is effective for treating melanoma. A 10% increase mouse survival following NRG-1 treatment indicates that the NRG-1 fragment is effective for increasing subject survival.

Example 13

Method of Preventing or Treating a Melanoma

This example illustrates a method of treating melanoma

A subject identified with an increased risk of acquiring melanoma or known to have melanoma is selected. A subject is administered a composition including the NRG-1 bioactive fragment identified by the methods of Example 11 at 50 ng/ml daily until tumor diameter has decreased by at least 10%. For prophylactic purposes, a subject applies the composition at least an hour prior to UV exposure. If subject is chronically exposed to UV, the subject applies the composition daily for an indefinite period of time.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

---

We claim:

1. A method of increasing pigmentation of a melanocyte in a subject, comprising:
    contacting the melanocyte of the subject with an effective amount of a type I neuregulin-1 (NRG-1) peptide or fragment thereof comprising a calcium-binding EGF domain that increases neuregulin-1 (NRG-1) activity thereby increasing pigmentation of the melanocyte, wherein contacting the melanocyte comprises local administration of the effective amount of the NRG-1 peptide or fragment thereof which comprise the calcium-binding EGF domain.

2. The method of claim 1, wherein increasing melanocyte pigmentation reduces UV skin damage.

3. The method of claim 1, wherein the administration comprises topical administration.

4. A method of reducing ultraviolet (UV) skin damage in a subject, comprising:
    selecting a subject having or at risk for UV skin damage; and
    administering locally to the subject an effective amount of a type I neuregulin-1 (NRG-1) peptide or fragments thereof comprising a calcium-binding EGF domain that increases NRG-1 activity as compared to NRG-1 activity in the absence of the agent, thereby increasing proliferation of the melanocyte and reducing UV skin damage in the subject.

5. The method of claim 4, wherein the method is for reducing the occurrence of skin cancer.

6. The method of claim 4, wherein the administration comprises topical administration.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide sequence for human
      ERBB2

<400> SEQUENCE: 1
acagtggcat ctgtgagctg                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide sequence for human
      ERBB2

<400> SEQUENCE: 2
agcagaggtg ggtgttatgg                                              20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide sequence for NRG-1

<400> SEQUENCE: 3
ctgtgtgaat ggagggagt                                               20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide sequence for NRG-1

<400> SEQUENCE: 4
```
gctttttccg ctgtttcttg                                           20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide sequence for GADPH

<400> SEQUENCE: 5
accacagtcc atgccatcac                                           20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide sequence for GADPH

<400> SEQUENCE: 6
tccaccaccc tgttgctgta                                           20

<210> SEQ ID NO 7
<211> LENGTH: 645
<212> TYPE: PRT
<213> ORGANISM: Homo sapiens

<400> SEQUENCE: 7

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Gln Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys His Leu Gly Ile Glu Phe Met Glu Ala
225                 230                 235                 240

```
Glu Glu Leu Tyr Gln Lys Arg Val Leu Thr Ile Thr Gly Ile Cys Ile
                245                 250                 255
Ala Leu Leu Val Val Gly Ile Met Cys Val Val Ala Tyr Cys Lys Thr
            260                 265                 270
Lys Lys Gln Arg Lys Lys Leu His Asp Arg Leu Arg Gln Ser Leu Arg
        275                 280                 285
Ser Glu Arg Asn Asn Met Met Asn Ile Ala Asn Gly Pro His His Pro
    290                 295                 300
Asn Pro Pro Pro Glu Asn Val Gln Leu Val Asn Gln Tyr Val Ser Lys
305                 310                 315                 320
Asn Val Ile Ser Ser Glu His Ile Val Glu Arg Glu Ala Glu Thr Ser
                325                 330                 335
Phe Ser Thr Ser His Tyr Thr Ser Thr Ala His His Ser Thr Thr Val
            340                 345                 350
Thr Gln Thr Pro Ser His Ser Trp Ser Asn Gly His Thr Glu Ser Ile
        355                 360                 365
Leu Ser Glu Ser His Ser Val Ile Val Met Ser Ser Val Glu Asn Ser
    370                 375                 380
Arg His Ser Ser Pro Thr Gly Gly Pro Arg Gly Arg Leu Asn Gly Thr
385                 390                 395                 400
Gly Gly Pro Arg Glu Cys Asn Ser Phe Leu Arg His Ala Arg Glu Thr
                405                 410                 415
Pro Asp Ser Tyr Arg Asp Ser Pro His Ser Glu Arg Tyr Val Ser Ala
            420                 425                 430
Met Thr Thr Pro Ala Arg Met Ser Pro Val Asp Phe His Thr Pro Ser
        435                 440                 445
Ser Pro Lys Ser Pro Pro Ser Glu Met Ser Pro Pro Val Ser Ser Met
    450                 455                 460
Thr Val Ser Met Pro Ser Met Ala Val Ser Pro Phe Met Glu Glu Glu
465                 470                 475                 480
Arg Pro Leu Leu Leu Val Thr Pro Pro Arg Leu Arg Glu Lys Lys Phe
                485                 490                 495
Asp His His Pro Gln Gln Phe Ser Ser Phe His Asn Pro Ala His
            500                 505                 510
Asp Ser Asn Ser Leu Pro Ala Ser Pro Leu Arg Ile Val Glu Asp Glu
            515                 520                 525
Glu Tyr Glu Thr Thr Gln Glu Tyr Glu Pro Ala Gln Glu Pro Val Lys
    530                 535                 540
Lys Leu Ala Asn Ser Arg Ala Lys Arg Thr Lys Pro Asn Gly His
545                 550                 555                 560
Ile Ala Asn Arg Leu Glu Val Asp Ser Asn Thr Ser Ser Gln Ser Ser
                565                 570                 575
Asn Ser Glu Ser Glu Thr Glu Asp Glu Arg Val Gly Glu Asp Thr Pro
            580                 585                 590
Phe Leu Gly Ile Gln Asn Pro Leu Ala Ala Ser Leu Glu Ala Thr Pro
        595                 600                 605
Ala Phe Arg Leu Ala Asp Ser Arg Thr Asn Pro Ala Gly Arg Phe Ser
    610                 615                 620
Thr Gln Glu Glu Ile Gln Ala Arg Leu Ser Ser Val Ile Ala Asn Gln
625                 630                 635                 640
Asp Pro Ile Ala Val
                645
```

<210> SEQ ID NO 8
<211> LENGTH: 3092
<212> TYPE: DNA
<213> ORGANISM: Homo sapiens

<400> SEQUENCE: 8

```
gaggccaggg gagggtgcga aggaggcgcc tgcctccaac ctgcgggcgg gaggtgggtg      60
gctgcgggc aattgaaaaa gagccggcga ggagttcccc gaaacttgtt ggaactccgg     120
gctcgcgcg aggccaggag ctgagcggcg gcggctgccg gacgatggga gcgtgagcag     180
gacggtgata acctctcccc gatcgggttg cgagggcgcc gggcagaggc caggacgcga     240
gccgccagcg gtgggaccca tcgacgactt cccggggcga caggagcagc cccgagagcc     300
agggcgagcg cccgttccag gtggccggac cgcccgccgc gtccgcgccg cgctccctgc     360
aggcaacggg agacgccccc gcgcagcgcg agcgcctcag cgcggccgct cgctctcccc     420
ctcgagggac aaacttttcc caaacccgat ccgagccctt ggaccaaaact cgcctgcgcc     480
gagagccgtc cgcgtagagc gctccgtctc cggcgagatg tccgagcgca agaaggcag     540
aggcaaaggg aagggcaaga agaaggagcg aggctccggc aagaagccgg agtccgcggc     600
gggcagccag agcccagcct tgcctccccg attgaaagag atgaaaagcc aggaatcggc     660
tgcaggttcc aaactagtct tcggtgtgaa accagttctg aatactcctc tctcagattc     720
aagtggttca agaatgggaa tgaattgaat cgaaaaaaca aaccacaaaa tatcaagata     780
caaaaaagc cagggaagtc agaacttcgc attaacaaag catcactggc tgattctgga     840
gagtatatgt gcaaagtgat cagcaaatta ggaaatgaca gtgcctctgc caatatcacc     900
atcgtggaat caaacgagat catcactggt atgccagcct caactgaagg agcatatgtg     960
tcttcagagt ctcccattag aatatcagta ccacagaag gagcaaatac ttcttcatct    1020
acatctacat ccaccactgg gacaagccat cttgtaaaat gtgcggagaa ggagaaaact    1080
ttctgtgtga atggagggga gtgcttcatg gtgaaagacc tttcaaaccc ctcgagatac    1140
ttgtgcaagt gcccaaatga gtttactggt gatcgctgcc aaaactacgt aatggccagc    1200
ttctacaagc atcttgggat tgaatttatg gaggcggagg agctgtacca gaagagagtg    1260
ctgaccataa ccggcatctg catcgcccctc cttgtggtcg gcatcatgtg tgtggtggcc    1320
tactgcaaaa ccaagaaaca gcggaaaaag ctgcatgacc gtcttcggca gagccttcgg    1380
tctgaacgaa acaatatgat gaacattgcc aatgggcctc ccatcctaa cccaccccc     1440
gagaatgtcc agctggtgaa tcaatacgta tctaaaaacg tcatctccag tgagcatatt    1500
gttgagagag aagcagagac atccttttcc accagtcact atacttccac agcccatcac    1560
tccactactg tcacccagac tcctagccac agctggagca acggacacac tgaaagcatc    1620
ctttccgaaa gccactctgt aatcgtgatg tcatccgtag aaaacagtag gcacagcagc    1680
ccaactgggg gccaagagg acgtcttaat ggcacaggag ccctcgtga atgtaacagc    1740
ttcctcaggc atgccagaga aacccctgat tcctaccgag actctcctca tagtgaaagg    1800
tatgtgtcag ccatgaccac cccggctcgt atgtcacctg tagatttcca cacgccaagc    1860
tcccccaaat cgccccttc ggaaatgtct ccacccgtgt ccagcatgac ggtgtccatg    1920
ccttccatgg cggtcagccc cttcatggaa gaagagagac tctacttct cgtgacacca    1980
ccaaggctgc gggagaagaa gtttgaccat caccctcagc agttcagctc cttccaccac    2040
aaccccgcgc atgacagtaa cagcctccct gctagccccct tgaggatagt ggaggatgag    2100
gagtatgaaa cgacccaaga gtacgagcca gcccaagagc ctgttaagaa actcgccaat    2160
```

-continued

```
agccggcggg ccaaaagaac caagcccaat ggccacattg ctaacagatt ggaagtggac    2220
agcaacacaa gctcccagag cagtaactca gagagtgaaa cagaagatga aagagtaggt    2280
gaagatacgc ctttcctggg catacagaac ccctggcag ccagtcttga ggcaacacct     2340
gccttccgcc tggctgacag caggactaac ccagcaggcc gcttctcgac acaggaagaa    2400
atccaggcca ggctgtctag tgtaattgct aaccaagacc ctattgctgt ataaaaccta    2460
aataaacaca tagattcacc tgtaaaactt tattttatat aataaagtat tccaccttaa    2520
attaaacaat ttatttatt ttagcagttc tgcaaataga aacaggaaa aaaacttta      2580 taaattaaat atatgtatgt aaaaatgtgt tatgtgccat atgtagcaat ttttacagt    2640 atttcaaaac gagaaagata tcaatggtgc ctttatgtta tgttatgtcg agagcaagtt   2700
ttgtacagtt acagtgattg cttttccaca gtatttctgc aaaacctctc atagattcag   2760
tttttgctgg cttcttgtgc attgcattat gatgttgact ggatgtatga tttgcaagac   2820
ttgcaactgt ccctctgttt gcttgtagta gcacccgatc agtatgtctt gtaatggcac   2880
atccatccag atatgcctct cttgtgtatg aagttttctt tgctttcaga atatgaaatg   2940
agttgtgtct actctgccag ccaaaggttt gcctcattgg gctctgagat aatagtagat   3000
ccaacagcat gctactatta aatacagcaa gaaactgcat taagtaatgt taaatattag   3060
gaagaaagta atactgtgat ttaaaaaaaa ct                                 3092
```

<210> SEQ ID NO 9
<211> LENGTH: 32
<212> TYPE: PRT
<213> ORGANISM: Artificial Sequence
<220> FEATURE:
<223> OTHER INFORMATION: synthetic peptide

<400> SEQUENCE: 9

Cys Val Asn Gly Gly Glu Cys Phe Met Val Lys Asp Leu Ser Asn Pro
1               5                   10                  15

Ser Arg Tyr Leu Cys Lys Cys Gln Pro Gly Phe Thr Gly Ala Arg Cys
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: synthetic peptide

<400> SEQUENCE: 10

Cys Val Asn Gly Gly Glu Cys Phe Met Val Lys Asp Leu Ser Asn Pro
1               5                   10                  15

Ser Arg Tyr Leu Cys Lys Cys Pro Asn Glu Phe Thr Gly Asp Arg Cys
            20                  25                  30

<210> SEQ ID NO 11
<211> LENGTH: 71
<212> TYPE: PRT
<213> ORGANISM: Artificial Sequence
<220> FEATURE:
<223> OTHER INFORMATION: synthetic peptide

<400> SEQUENCE: 11

Thr Ser His Leu Val Lys Cys Ala Glu Lys Glu Lys Thr Phe Cys Val
1               5                   10                  15

Asn Gly Gly Glu Cys Phe Met Val Lys Asp Leu Ser Asn Pro Ser Arg

```
                    20                  25                  30
Tyr Leu Cys Lys Cys Pro Asn Glu Phe Thr Gly Asp Arg Cys Gln Asn
                35                  40                  45

Tyr Val Met Ala Ser Phe Tyr Lys His Leu Gly Ile Glu Phe Met Glu
            50                  55                  60

Ala Glu Glu Leu Tyr Gln Lys
65                  70
```